(12) United States Patent
Waugh et al.

(10) Patent No.: US 10,503,875 B2
(45) Date of Patent: Dec. 10, 2019

(54) MEDICATION ADMINISTRATION APPARATUS

(71) Applicant: ACEAGE INC., Guelph (CA)

(72) Inventors: Donald Craig Waugh, Oakville (CA); Donald Spencer Waugh, Guelph (CA); Evan David Cook, Abbotsford (CA); Nicholas James Reeves, Vancouver (CA); Nikita Mouline, Vancouver (CA); Trevor Uittenbosch, Abbotsford (CA)

(73) Assignee: AceAge Inc., Burlington, Ontario (CA)

(*) Notice: Subject to any disclaimer, the term of this patent is extended or adjusted under 35 U.S.C. 154(b) by 29 days.

(21) Appl. No.: 15/079,907

(22) Filed: Mar. 24, 2016

(65) Prior Publication Data

US 2016/0324727 A1 Nov. 10, 2016

Related U.S. Application Data

(60) Provisional application No. 62/157,858, filed on May 6, 2015.

(51) Int. Cl.
*A61J 7/04* (2006.01)
*G06F 19/00* (2018.01)

(52) U.S. Cl.
CPC ........ *G06F 19/3462* (2013.01); *A61J 7/0418* (2015.05); *G06F 19/3418* (2013.01); *A61J 2200/30* (2013.01)

(58) Field of Classification Search
CPC . A61J 7/0418; A61J 2200/30; G06F 19/3462; G06F 19/3418
USPC ................................. 700/231–244
See application file for complete search history.

(56) References Cited

U.S. PATENT DOCUMENTS

| 6,394,306 B1* | 5/2002 | Pawlo | A61J 7/0409 221/15 |
| 8,196,774 B1* | 6/2012 | Clarke | A61J 7/0409 221/13 |
| 9,117,010 B2* | 8/2015 | Feldman | G06F 19/32 |
| 2005/0049747 A1* | 3/2005 | Willoughby | A61J 7/0084 700/232 |
| 2007/0173971 A1* | 7/2007 | Richardson | G06F 19/3462 700/231 |

(Continued)

*Primary Examiner* — Michael Collins
(74) *Attorney, Agent, or Firm* — Stuart L. Wilkinson

(57) ABSTRACT

The present disclosure relates to a medication adherence administration and monitoring system. An apparatus for managing medication adherence by a patient is provided, the apparatus comprising: a dispensing device configured for communication with a medication administration system, the dispensing device designed for dispensing medication stored within the dispensing device to the patient; a control system for controlling the dispensing device based, at least in part, on command instructions provided by the medication administration system, and issuing commands to dispense medication based on the satisfaction of one or more pre-determined conditions provided by the medication administration system; and an alert system configured for alerting the patient when medication should be dispensed and configured to receive an indication from the patient verifying the consumption of medication, the alert system communicating to the control system that the medication has been dispensed and consumed.

31 Claims, 19 Drawing Sheets

(56) References Cited

U.S. PATENT DOCUMENTS

| | | | |
|---|---|---|---|
| 2011/0208348 A1* | 8/2011 | Bogue | A61B 5/0095 700/233 |
| 2011/0288880 A1* | 11/2011 | Waugh | G06F 19/3462 705/2 |
| 2012/0002042 A1* | 1/2012 | Okuma | A61J 7/02 348/135 |
| 2012/0083666 A1* | 4/2012 | Waugh | A61J 7/0084 600/300 |
| 2012/0101630 A1* | 4/2012 | Daya | G06F 19/325 700/231 |
| 2012/0310410 A1* | 12/2012 | Adams | E05G 1/04 700/237 |
| 2013/0282163 A1* | 10/2013 | Brown | G07F 17/0092 700/215 |
| 2015/0019009 A1* | 1/2015 | Feldman | G06F 19/32 700/237 |

* cited by examiner

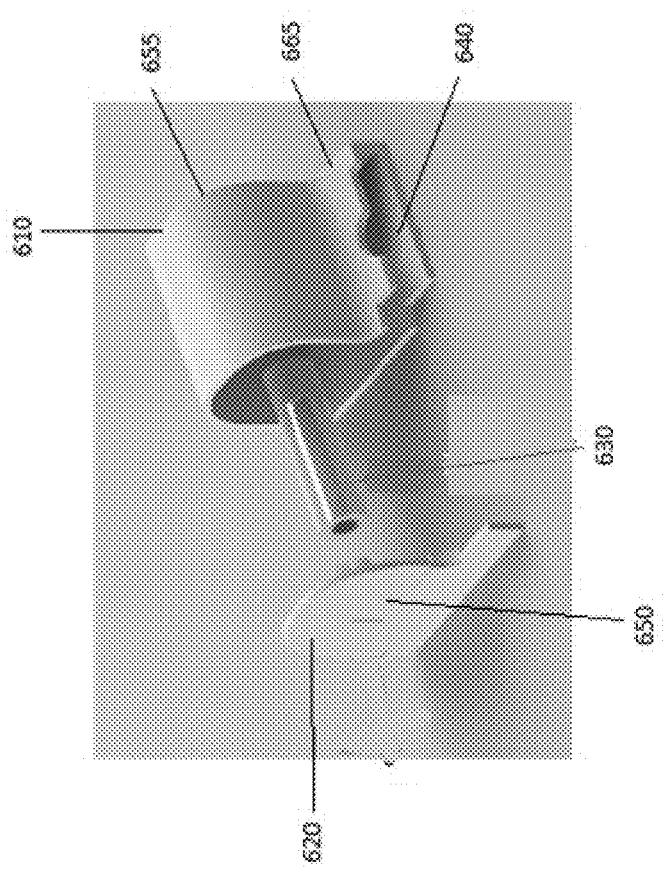
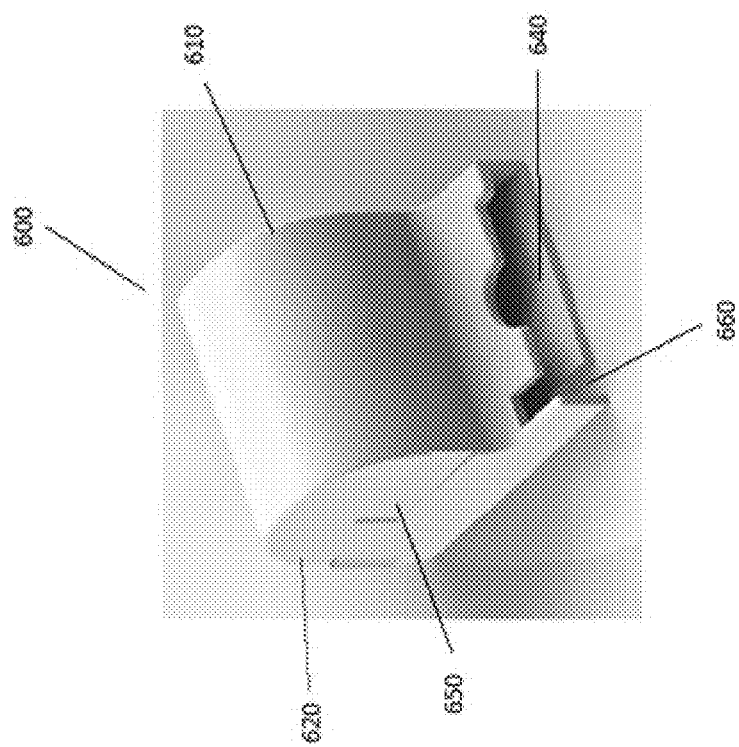
FIG. 6B
FIG. 6A

MEDICATION ADMINISTRATION APPARATUS

CROSS-REFERENCE TO RELATED APPLICATIONS

This application claims the benefit of U.S. Patent Application No. 62/157,858, filed May 6, 2015, the contents of which are hereby incorporated by reference in their entirety.

TECHNICAL FIELD

This disclosure relates generally to the administration of medication, and more particularly, to apparatuses and methods for managing the administration of medication.

BACKGROUND

Medication adherence issues account for a significant amount of unnecessary expenditures and may result in suboptimal healthcare outcomes and/or problems for patients.

Adherence to medication intake (the administering of the correct dosage at the correct date and time) has been a significant challenge in the healthcare field. While there may be a number of products designed to promote adherence to medication, these products have not been very effective. For example, a patient may be provided with several pharmaceutical products for consumption at various times of the day, with the timing of the intake of the products, as well as the dosages being important (e.g., based on a dosing regimen) from a pharmacokinetic perspective (e.g., maintaining a therapeutic dosage level in the bloodstream).

Deviating from the particular dosage regimen may have adverse effects on the health of a patient (e.g., straying outside a therapeutic range, straying into a range having toxic side effects), and may also result in increased costs and/or the proliferation of medicines that should have otherwise been consumed by patients (e.g., proliferation of hydrocodone).

The failure of patients to adhere to their medication regime properly can also be detrimental to clinical research. Participants in phase 3 and 4 drug trials are simply being trust to take their medication properly and report their results at the end of the trial. Without any existing measures in place to document how the patients in these trials are taking their medication, non-compliant patients may be included in the data set of these trials. This inaccurately reports the effects of the medication, and can result in the medication not achieving regulatory approval.

Some devices and techniques require manual administration and loading by the patient, a care giver, professional support worker or a pharmacist. Unsurprisingly, manual administration has led to devices that are prone to error and adherence failure, with an inability to conduct practical monitoring of patient adherence. Further, the devices may also be loaded incorrectly, causing potential harm to a patient (e.g., a practitioner unintentionally loads a device with the wrong dosage or type of medication).

At the present time, compliance data, if it is recorded at all, is being documented manually in a very unscientific way. If a patient has pills remaining at the end of a trial, they are averaged out to get a compliance percentage. This may be documented using Electronic Data Capture Applications such as InForm by Oracle, MediData Rave by MediData Solutions, and iDataFax by Clinical DataFax Systems. Some trials still use paper and fax-based methods. In both cases, these may require manual entry, and the data is being recorded after-the-fact—often long after the medication has been taken, which may lead to inaccuracies in the data, and not being able to guarantee proper drug compliance.

A significant portion of the population is being treated for multiple chronic diseases. In Canada, approximately one third of the population (12 million) is on at least one chronic medication. Of these 12 million Canadians, 3 million are over the age of 65 and are beginning to face the challenges of managing multiple medications. Non-adherence is a problem across all ages, for example, for children with risks from asthma, cancer, organ transplants, etc.

SUMMARY

In various aspects, the disclosure provides systems, methods and devices for managing a patient's adherence to medication, and logic structures such as machine-executable coded instruction sets for implementing such systems, devices, and methods. Some embodiments of the present invention may automate data collection during the administration of medication to one or more patients, resulting in the data being less likely to be missed or inaccurately stored.

In this respect, before describing some example embodiments of the invention in detail, it is to be understood that the invention is not limited in its application to the details of construction and to the arrangements of the components set forth in the following description or illustrated in the drawings. The invention is capable of being embodied in other forms and of being practiced and carried out in various ways. Also, it is to be understood that the phraseology and terminology employed herein are for the purposes of general description of various embodiments of the invention and should not be regarded as having a limiting effect on the invention.

According to one aspect of the present invention, there is provided an apparatus for managing medication adherence by a patient, the apparatus comprising: a dispensing device configured for communication with a medication administration system, the dispensing device designed for dispensing medication stored within the dispensing device to the patient; a control system for controlling the dispensing device based, at least in part, on command instructions provided by the medication administration system, and issuing commands to dispense medication based on the satisfaction of one or more pre-determined conditions provided by the medication administration system; and an alert system configured for alerting the patient when medication should be dispensed and configured to receive an indication from the patient verifying the consumption of medication, the alert system communicating to the control system that the medication has been dispensed and consumed.

According to one aspect of the present invention, there is provided an apparatus for managing adherence to medication by a patient, the apparatus comprising: a processor; a memory storing a medication schedule; an alert system configured to notify the patient to take medication, wherein the alert system is activated based on the medication schedule; a dispensing unit configured to dispense at least one pouch containing one or more medications, each of the at least one pouches having displayed thereon a machine-readable indicia; and an input configured to receive from a user an instruction to dispense at least one of the at least one pouches, wherein the instruction to dispense deactivates the alert system and causes a camera to scan the indicia on each pouch to be dispensed, wherein the processor is configured to extract scheduling information from the scanned indicia and compare the extracted scheduling information to the medication schedule; and wherein the at least one of the at least one pouches is dispensed by the dispensing device if the extracted scheduling information matches the medication schedule.

According to another aspect of the invention, there is provided a method of managing adherence to medication by a patient, the method comprising: receiving a medication schedule; activating an alert system based on the medication schedule; receiving an instruction from a user to dispense, from a dispensing unit, at least one pouch containing one or more medications, each of said at least one pouches having displayed thereon a machine-readable indicia; responsive to receiving the instruction to dispense, deactivating the alert system; scanning the indicia of each of the at least one pouches to be dispensed; extracting scheduling information from the scanned indicia; comparing the extracted scheduling information to the medication schedule; and dispensing the at least one pouch if the extracted scheduling information matches the medication schedule.

According to another aspect of the present invention, there is provided a non-transitory computer-readable storage medium having stored thereon computer-executable instructions that, when executed by a processor, cause the processor to perform the method as described herein.

Many further features and combinations thereof concerning embodiments described herein will be apparent to those skilled in the art following a reading of the present disclosure.

BRIEF DESCRIPTION OF THE DRAWINGS

In the figures, example embodiments are illustrated. It is to be expressly understood that the description and figures are only for the purpose of illustration of some embodiments of the invention and as an aid to understanding various concepts disclosed herein.

Embodiments will now be described, by way of example only, with reference to the attached figures, in which:

FIGS. 6A and 6B are perspective and exploded views, respectively, of an example cartridge for storing pouch packaging, according to some embodiments.

DETAILED DESCRIPTION

Figure 1:
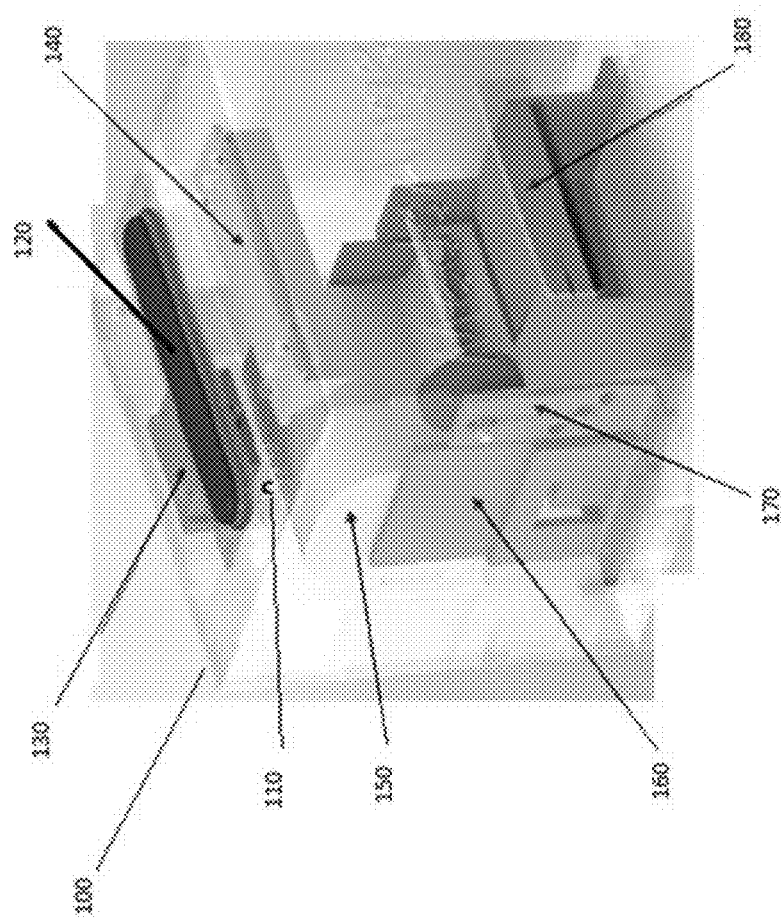
FIG. 1 is a perspective view of an example embodiment of an apparatus for dispensing medication.

Various embodiments of methods, systems, and apparatus are described herein by way of reference to the drawings, which are intended to be examples and not to be limiting on the scope of the invention.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

According to some embodiments, a schedule that is used to create pouch packaging of medication may be communicated to an adherence monitoring platform and to a device (e.g., a smart phone) owned by the patient to deliver a medication reminder service. In some embodiments, the schedule is communicated from a pharmacy or pharmacy management system to the mobile device (e.g. the smart phone). With the medication schedule, the reminder service may synchronize with the medication pouches by scanning barcodes on the pouches to ensure the correct medication is being taken on the correct date and time. In another aspect, the patient or authorized user confirms that the medication has been taken.

A dispensing unit may integrate with a cartridge which is designed for easy and reliable loading of the medication pouch packaging, and may provide for the optimal flow of the pouch packages. The cartridge may be designed to overcome challenges related to the moving of irregularly shaped pouch packaging inside the cartridge for conveyance into and through the dispensing device through to the dispensing of the pouch medications to the patient. It is important that the pouch packaging be configured for resistance to jamming, tearing or otherwise corrupting inside the dispensing devices, as this may result in a failure to dispense medicine to the patient. In some embodiments, a specific mechanism may be provided to move the packaging through the dispensing unit which is supplemented with monitoring and measuring sensors inside the dispensing device to further ensure reliability.

Some embodiments of the invention may establish a platform for managing a patient's treatment for diseases with medication management being one aspect. Managing adherence to a medication schedule is important, as is measuring the patient's response to their medications. Such measurements may provide insight into whether the disease is being managed and under control as per the expected response to the medication.

Measurement is not only a control mechanism. Measurement of the patient's response to the medication may also be used for feedback and reward systems where adherence to prescribed medicines as well as life style changes create a platform for reporting back to the patient on their success in the management of their disease(s) and alert the patient if they are not responding so that corrective intervention can be taken in a timely manner.

While one of the purposes of the methods and systems described herein is their use by patients for facilitating compliance and adherence to drug prescriptions, the disclosed systems and methods may also offer additional benefits to third parties in the health care system which are not easily or readily available from known systems in place today. Some examples of these additional benefits include:

For pharmacists, their role may extend beyond being a purveyor of medications to being the professional responsible for the patient's management of their disease states. The system may automate a system of care that starts with medication which is augmented with monitoring and measurement devices and systems that the pharmacist provides to support their patients to manage their diseases.

For pharmaceutical companies, such a system can be used for phase three and four clinical trials, post market surveillance as well as support patients for compliance that use their drugs.

For researchers, the system may enable a platform for collecting feedback from patients in a systematic and private way.

For secondary care providers, the platform can be a delivery or order platform for services to patients. For example, in addition to drugs, diabetes is also managed by diet. The disclosed systems and methods could, in some embodiments, allow for dieticians to deliver counseling and for grocers to deliver groceries that meet the needs of the diabetic patient.

The provisioning of medicine may include various methodologies under which diseases are managed, including dosage regimens, timing, etc. The present disclosure provides various systems which may improve patient care, render adherence to prescribed medicine more likely, and provide improved management of disease states.

One or more apparatuses and/or devices may be provided that aid in the dispensing, monitoring and/or tracking of patient adherence to medication regimens and/or the consumption/use of medication. For example, pouch packaging technology may be leveraged where compartmentalized pouch packages may be utilized to provide patients with pouches that are easy to view, thereby facilitating the patient in remembering to take the medication. Such technology, for example, may be developed for use in long term care and hospital environments.

Some embodiments of the disclosed apparatuses may be configured such that various features may enable the ordinary user to reload the apparatus with more medication pouch packaging, for example, through having a removable cartridge structure that is configured to cooperate with the conveyance system.

Various electro/mechanical/structural aspects may be included which provide for the cooperation of various structural features of the apparatus, providing a streamlined, effective design that may be designed for durability and reduced errors in operation.

Medication Administration Device

As illustrated in FIG. 1, there is disclosed an example embodiment of a device 100 for dispensing pouch packaging of medication. In some embodiments, there is a bar code reader camera 130 and a button 120 to turn off the alarm 110 and confirm the taking of the medication, a mirror 140 for reflecting light to facilitate reading the bar code of a medication pouch package, a medication cartridge 150 inserted into a cartridge receiver 160, a roller assembly 170 and a scanning table 180.

Figures 3A, 3B:
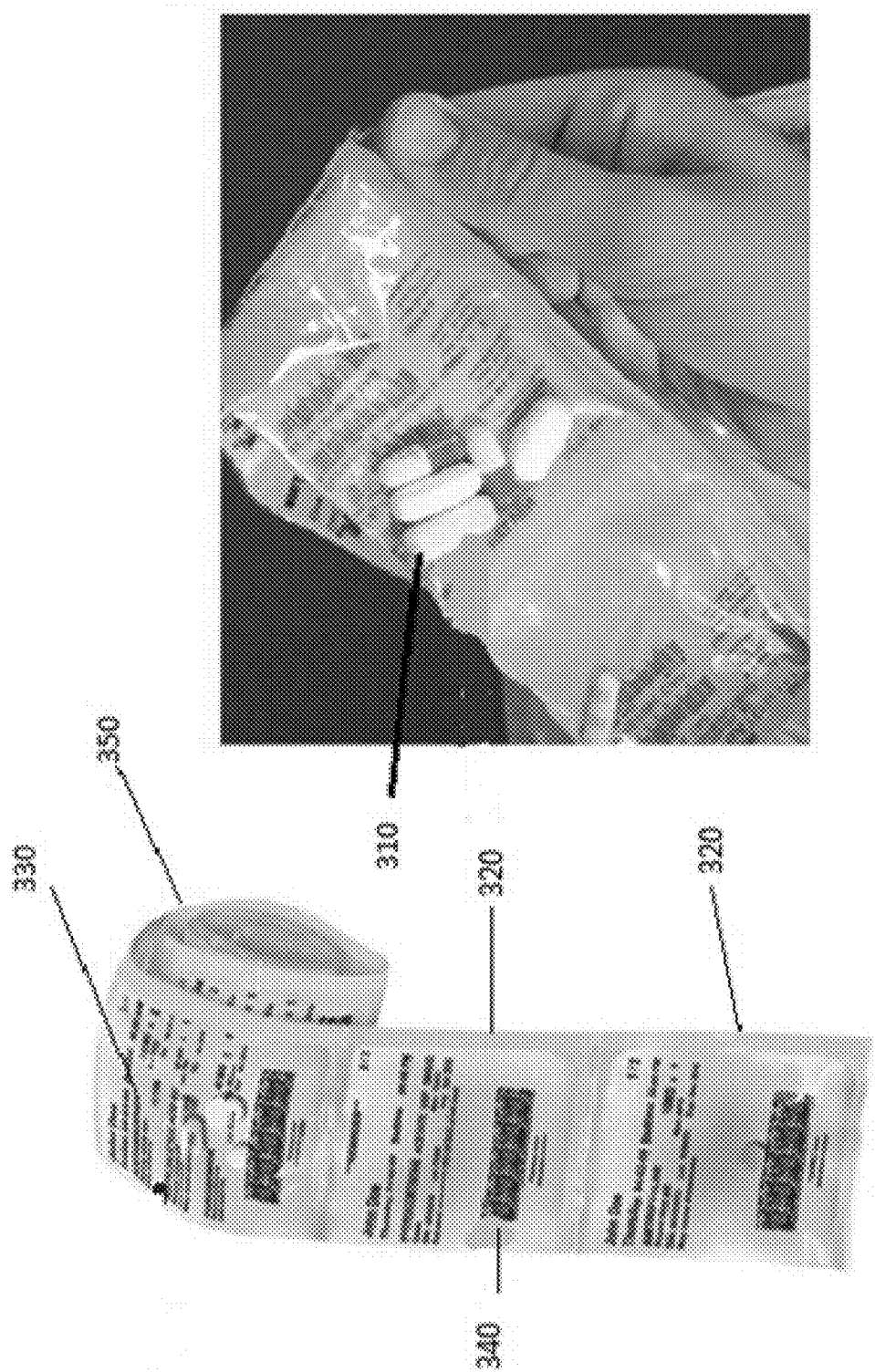
FIGS. 3A and 3B illustrate example embodiments of medication pouch packaging.

As shown in FIG. 3, pouch packaging organizes patient medications 310 based on various rules and/or groupings, for example, by date, by symptom, etc. Each pouch package 320 includes printed medication and patient information 330 including the patient name and the date and time to take the medication(s), and an identification of the medication which is stored in the pouch package 320. Such medication and patient information may be summarised in a machine readable indicia, such as a two dimensional bar code 340. Individual pouches 320 may also be attached to form a chain 350 of pouches.

As illustrated in FIGS. 6A and 6B, the pouch packaging may be loaded into a cartridge 600. The cartridge 600 may include a housing unit 610, a lid 620 and a spool 630 that is used to hold the pouch packaging 350. The cartridge lid 620 may also comprise one or more recesses 650 which may aid in securing the cartridge 600 within a receiver that has corresponding features for frictionally engaging with the recesses 650. The cartridge 600 can be sealed and be tamper or child proof. The loading of the pouch packaging 350 into the cartridge 600 is best illustrated in FIG. 7B (described below). The upper portion 655 of housing unit 610 may, in some embodiments, have a generally semicircular cross-section, with an additional lower portion 665 for dispensing the pouches having a generally rectangular cross-section.

Patient Workflow

Figure 2:
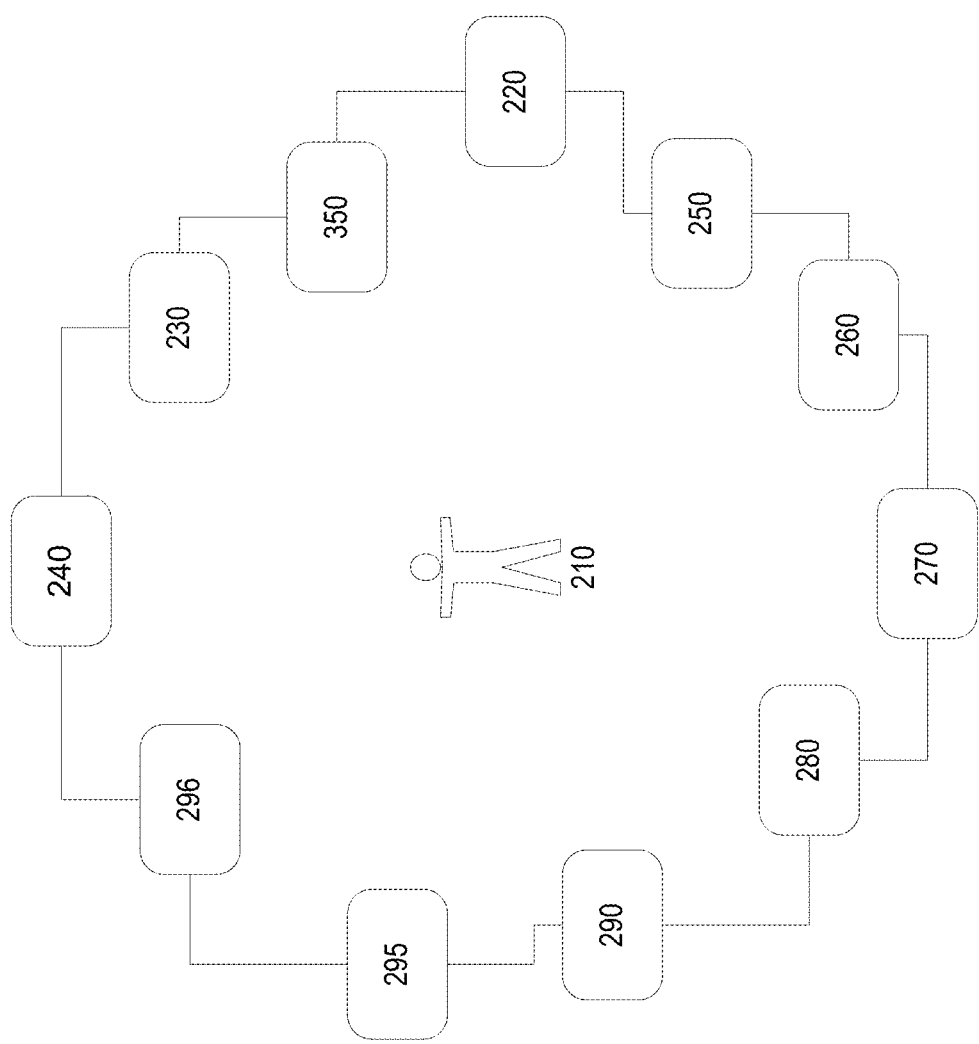
FIG. 2 is a workflow diagram for some embodiments of medication adherence and monitoring systems.

Referring to FIG. 2, a workflow diagram for medication management systems utilized to manage and/or administer various aspects of treatment in relation to medications is shown. The workflow 200 can be provided on various platforms and technologies.

Some embodiments provided in this disclosure provide a network of connected medication administration and disease monitoring devices in a medication adherence, support and monitoring system. An individual patient 210 may connect various computer terminals/connected devices 220 operable to access a network (e.g., intranets, the Internet, peer to peer systems) through various communication mediums (e.g., cellular, wireless, dialup). The network connection enables the transmission and reception of digital data by the network connected devices 220 and medication adherence, support and monitoring system, each of which may be operable in various ways.

A patient's 210 medication record 230 may be reviewed and tracked by a pharmacist to ensure the safety of the medication being taken. After such a review, a pharmacist may order and prepare the medications in pouch packaging as shown in FIG. 3.

The cartridge 600 loaded with pouch packaged medication 350 may be delivered to the patient for loading in to the device 100 or can be used manually as a medication dispensing cartridge.

For example, a patient using the device may be going out on a day trip or weekend and may not be able to take the device 100 with them.

In such cases, an override can be made available where the patient or a care giver can dispense pouches 320 for the days absent and use a manual adherence reminder method.

The device 100 may be connected to various network connected devices 220, including, for example, smart phones, mobile phones, tablets or computers. The schedule that was used to instruct the pouch packaging machine to prepare the pouch packaging 350 is communicated to the medication monitoring system and in turn, the schedule may be downloaded to the network connected devices 220. When the patient's medications are packaged in the pouch packaging cartridge 600, the cartridge 600 may be loaded into the patient's device 100.

When the cartridge 600 is loaded into the device 100, the device 100 may be configured to read the barcode 340 to confirm and/or ensure the synchronization of the pouch packaging 320 with the medication schedule.

When it is time to take the medication 310, an alarm 110 may be utilized to alert the patient that it is time to take the medication 310. When the patient responds, the patient may indicate that the alarm 110 should be turned off in various ways (e.g., by tapping a button 120 on the device 100) and the device 100 may dispense the pouches 320 containing the medications to be taken. Upon taking the medication 310, the patient will signal that they have taken the medication, for example, by tapping a button 120 on the device 100. Such confirmation may be recorded in the patient's medication record 240. Various features may be used to indicate that the alarm 110 has been turned off and adherence was confirmed. For example, an alarm light 110 may be lit with differing colours. In this example, the alarm light 110 can flash for added attention and may be accompanied by an audible alarm. The alarm 110 may also be incorporated into various devices and/or technologies, such as wearable devices, smartphones, and otherwise provide a signal even if the device is located from the patient to alert the patient.

Figure 10:
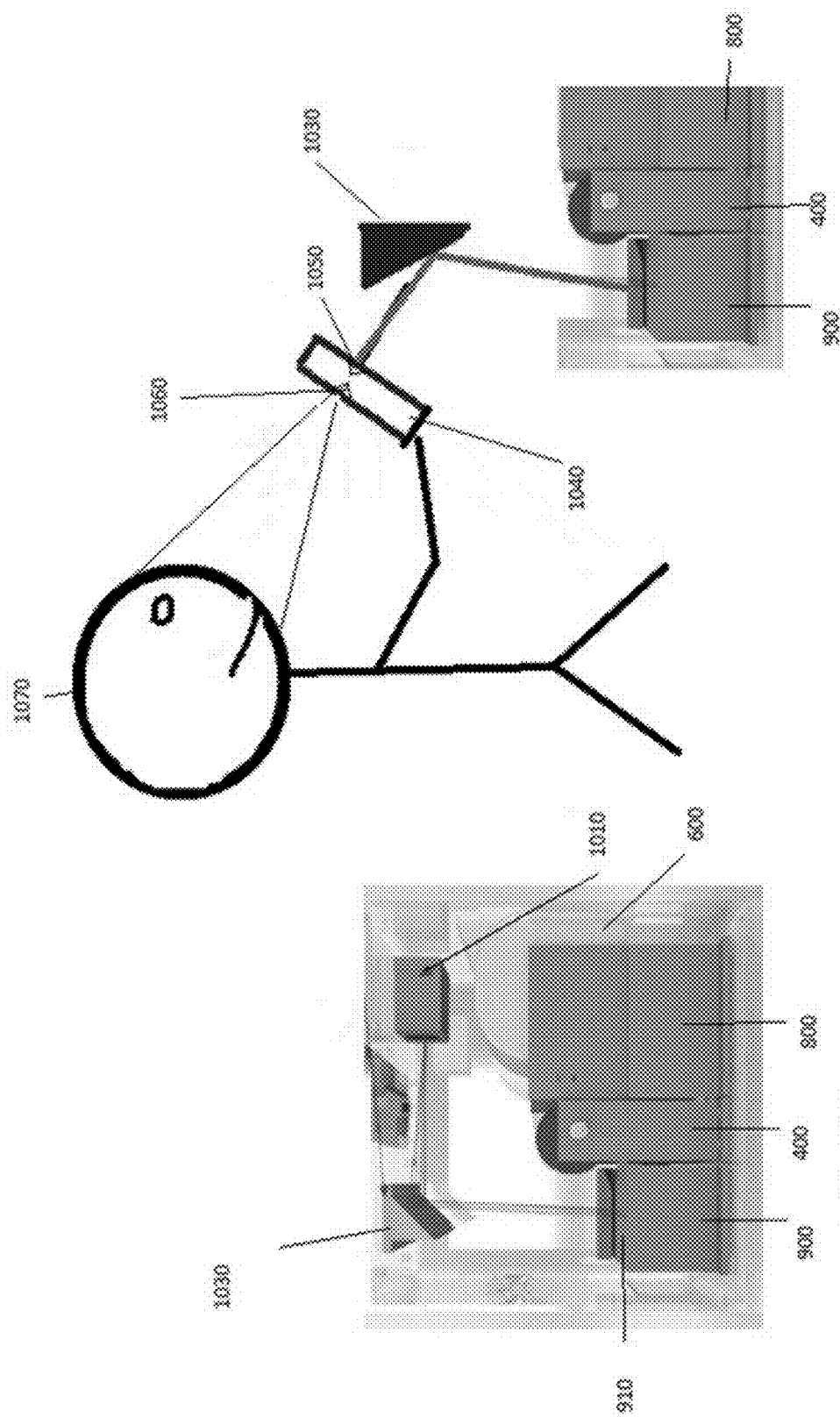
FIGS. 10A and 10B are side views of example embodiments of a dispensing apparatus which include a camera.

Confirmation that the medication has been taken by the patient can take many forms depending on various requirements (e.g., the needs of the patient, the drug type, legislation, healthcare facility policies). For methadone, for example, there may be a requirement that a person must witness a person ingesting their medicine. Such a process requiring a witness can be accomplished, for example, via a camera in the network connected device 220 (an example configuration is explained below in further detail with reference to FIG. 10). Using a network connected device 220, a person located in a counseling centre could connect with the patient and witness the ingestion. This same facility can also be used for other recalcitrant patients. Children can be a challenge, as well as patients who are handicapped and/or otherwise have learning challenges or disabilities. In these cases, a family member or support worker could also witness the ingesting of prescribed medication. Such witnessing may or may not need to be real time, and thus may or may not require the presence of a person. Such ingesting could also be captured by video as an enforcement or audit technique.

If a patient fails to turn off the alarm 110, a notification may be sent to the patient's family member, care giver etc. to alert them that intervention is required. Should a person not be available to intervene, then various signals may be communicated (e.g., an escalation order) will be made to escalate the matter, for example, to a call centre.

When a person is using the system manually, the confirmation of adherence will be conducted as part of the synchronization between the medication pouch 320 and a reminder schedule 250. When the reminder is set off on the network connected device 240, the patient will turn off the alarm 110, which in turn will turn on the bar code 340 reader feature. The reading of the bar code 340 will verify the pouch package 320 with the schedule 250 which can be assumed to be the record of confirmation.

To measure the patient's response to their medication the patient may be prompted to use a monitoring device 260 such as a blood pressure monitor, glucometer, lipidometer, peak flow monitor, etc. Men a patient takes such measurements the record will be added to the patient's record 240.

Based on the date/time collected from the device 100 and the patients monitoring device 260, symptom tracker reports 270 and progress reports 280 and inspirational messages 290 can be prepared and delivered to the patient via the device 100 or the network connected devices 220 or via email or other communication mechanism including paper or notices to care givers to instruct them to acknowledge and encourage the patient.

Should a patient not be adhering to their medication schedule or symptom measurements are demonstrating that the patient is not responding to their medication or that the medication is not effective for the patients disease state, the medication adherence support and monitoring system can alert a health care professional to converse with the patient 295 online or off-line, or intervention alerts 296 can be issued to health care professional or care givers to indicate that action is required.

In various cases, the patient's use of the device 100, the patient's measurement of the monitoring devices 260, symptom tracker reports 270 and progress reports 280 and inspirational messages 290, health care professional interaction with the patient 295 or intervention by the health care professional or care givers 296 can be recorded to the patient's medical record 240.

Components of a Medication Adherence, Support and Monitoring System

The present description describes some components of a medication adherence, support and monitoring system 500, which may provide various functionality for medication organization, memory aids for patients and external adherence monitoring.

The system 500 may leverage pouch packaging technology to automate the organization of medication into plastic strip pouch packaging which is stored, according to some embodiments, within a cartridge 600 specifically designed to include a child proof enclosure.

The cartridge 600 is designed to protect the medication 310 and medication pouches 320 in transport and at their final destination. The cartridge 600 is also designed to be used manually by an able bodied patient or for easy insertion into a device 100, which is another aspect of some embodiments.

Figure 5:
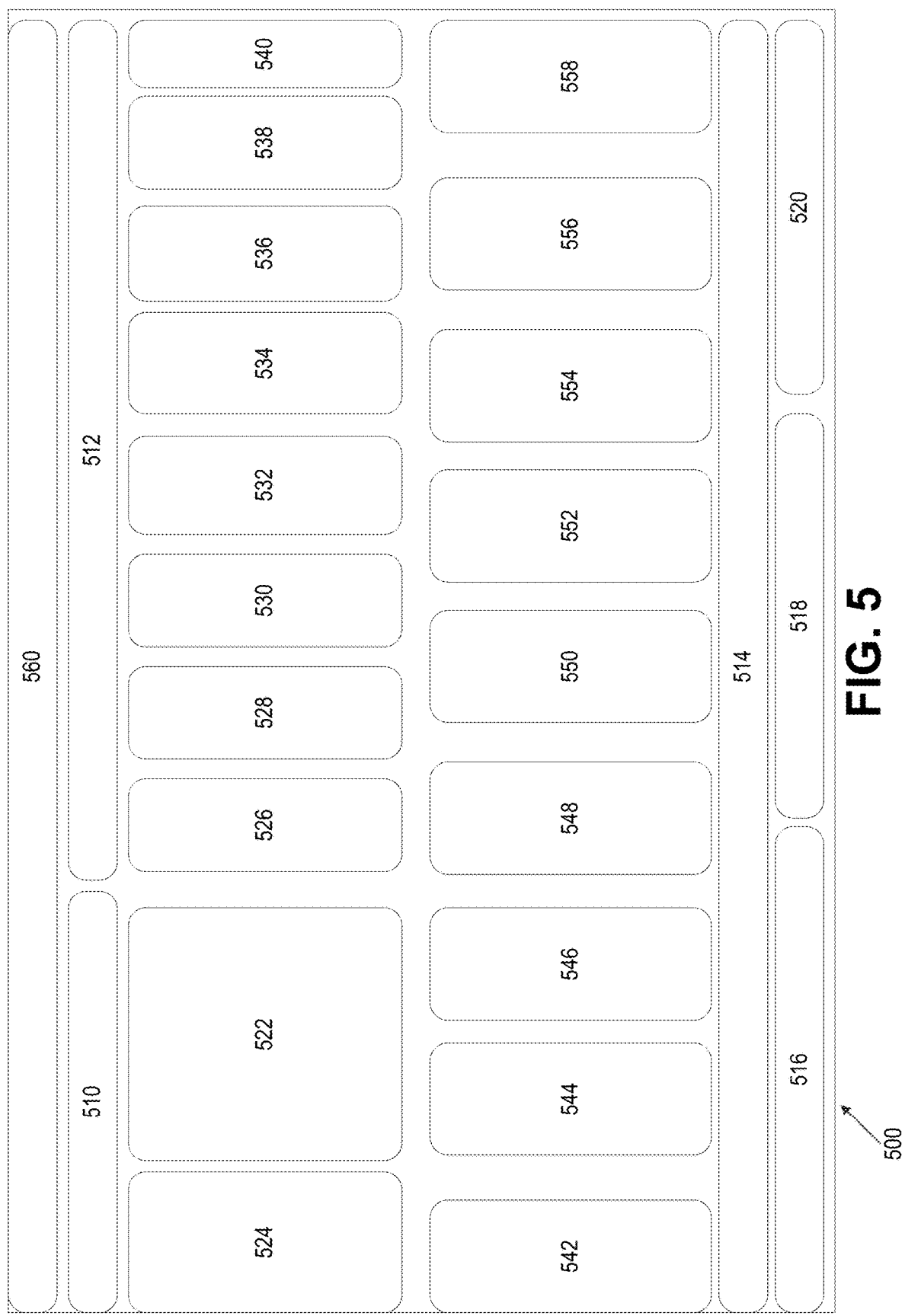
FIG. 5 illustrates the components of a medication adherence, support and monitoring system, which, in some embodiments, may be used to perform some or all of the functionality described herein.

FIG. 5 illustrates the components of a medication adherence, support and monitoring system, according to some embodiments.

Components of a medication adherence, support and monitoring system 500 may be provided for use and/or functionality defined for various roles (e.g., pharmacists, patients, partners). For example, a pharmacist interface 510 may be provided, and the pharmacists may be able to access the systems and view information provided by and tailor the patient interface 512 via the services layer 560, interacting with various partner systems 514 which includes, for example, pharmaceutical partners 516, care professionals and worker 518 and drug plan providers 520.

The pharmacist using, for example, a pharmacist interface 510 may provide medication reconciliation services 522 and the dispensing of patient pouch packaged medications 524. The patient interface 512 may interface with the system via a reminder service 526, the symptom monitor 528, the tracking service 530, the progress reporting service 532, the inspirational messages 534, the teachable moments 536, access to health care professionals 538, and interventions 540.

To deliver such services to the patient and the pharmacist, as well as partners, the following components, services and databases may be utilized, including a pharmacy management system 542, a multi-dose pouch packaging system 544, a patient medical record 546, cloud computing services 548, medication administration devices 550, monitoring devices 552, patient register, authentication and messaging services 554, network connected devices 556, and tele-health video services 558.

Medication Prescribing and Dispensing

Medication is prescribed by doctors and is dispensed by pharmacists. The document that authorizes the pharmacist to dispense medicine to the patient is called the prescription. This term is distinct from the use of the colloquial term "prescription" that patients use to describe their medicine purchase.

Some embodiments are designed to fit within the existing medicine prescribing and dispensing system.

When a pharmacist receives a prescription they are provided the authority to dispense and sell medicine to the patient. The dispensing of such medicine is made in a variety of ways with pill bottles being the primary packaging method.

However, a specialized method using a medication pouch packaging technology that packages prescribed medication by day and time to take such medicine may be provided. The ordering work flow for such packaging inside a pharmacy may be achieved by the pharmacy management system communicating the prescription order to a pouch packaging machine (not illustrated).

The pouch packaging machine, on receipt of the prescription order, creates the pouch packaging order to package medication for a patient which is designed to facilitate the administration of medicine to patients based on the prescription ordered by that patients doctor.

For such environments, pouch packaging 320 assists institutional staff in the management and administration of medicines 310 to patients.

A pouch packaging machine, such as those provided, for example, by Amerisource Bergin™, McKesson™, Talyst™, etc., packages patient medicines in plastic pouches 320 organized by day and time for the administration of medicines to patients. Each pouch 320 can hold a variety of different medicines 310 that should be taken by the patient at the specified date and time.

Each individual pouch 320 may be imprinted with information such as the patients name, date and time to take the medicines 330, a list of the medicines in the pouch package as well as a bar code 340.

The bar code 340 is a machine readable indicia representing the printed information. The pouches 320 are typically linked or physically connected together in a strip 350 in date and time order.

In some embodiments, institutional staff administer patient medicine 310 by reading the bar code or similar identifier on a patients wrist and the bar code 340 information on the pouch package 320. These readings may be recorded in an EMAR (Electronic Medication Administration Record).

There are a number of products that use pouch packaging for medication dispensing and in some cases adherence monitoring. These products include Dayamed™, Innospense™, and Vitaphone™, and a product that was patented by Christopher Willoughby but, because of its design and complexity, could not become a commercial success.

The first three aforementioned products are also complex and very costly, similar to the Willoughby device. As a result, they have not seen widespread adoption, as the costs may be prohibitive for the average consumer.

Furthermore, the aforementioned devices are limited in their use because they only offer one configuration for compliance purposes whereas the need in the market is much more diverse.

The pouch packaging 320 as illustrated in FIG. 3 can be designed for dispensing across various lengths of time but is typically configured for a two to four week duration, depending on a number of factors. Each pouch 320 may be imprinted with a machine readable indicia 340 (pouch identifier). The set of pouches 350 being dispensed for the patient would have a cartridge spool identifier associated with it, which would also be associated with a machine readable identifier (cartridge identifier). Generally, each pouch 320 is associated with a dosage (one or more medications to be taken at a specific time). A plurality of pouches 350 should be provided consistent with the sequence of doses in chronological order as prescribed by the doctor.

The schedule that is used to create the pouch packaging 350 as illustrated in FIG. 3 may be communicated by the pouch packaging system software to the Monitoring Server 552 and appropriate network connected device.

The cartridge 600 and pouch packaging 320 are provided such that once the pouch packaging 320 is loaded in the cartridge 600, and the cartridge 600 is loaded into the device 100, the device 100 dispenses the pouch 320 in the order defined by the prescription which is verified by the reminder schedule 250 that was derived from the pouch packaging order that packaged the medication for the patient. For each and every administration of a pouch 320 to a patient, the pouch 320, using the machine readable identifier 340, is checked against the prescribed schedule 250 to ensure the correct patient is getting the correct drugs(s) on the correct date and time.

The reminder system may also be configured to determine when a patient's medications 310 are going to run out or are running low. In some embodiments, pharmacy management systems 542 may be configured to monitor for reorders and repeats, and will send a new order to the pouch packaging system to manufacture a new set of pouch packages 350 for loading into the cartridge 600 which will be delivered to the patient's location. When the cartridge 600 which was previously inserted in the device 100 is emptied, the patient, family member, care worker etc. can easily remove the old cartridge 600 and load the new replenishment cartridge 600 into the device 100.

Medication Administration Device Components

Figure 4C:
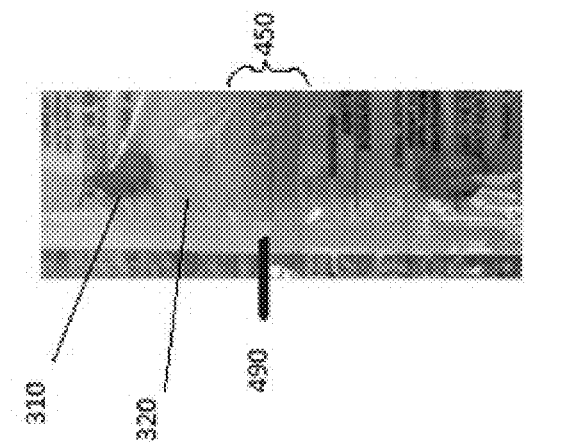
FIGS. 4A, 4B and 4C illustrate an example roller mechanism for moving pouch packaging, according to some embodiments.
Figure 4B:
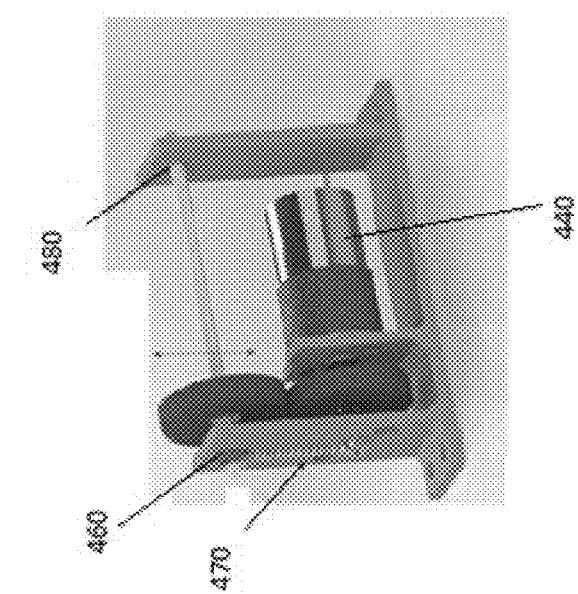
Figure 4A:
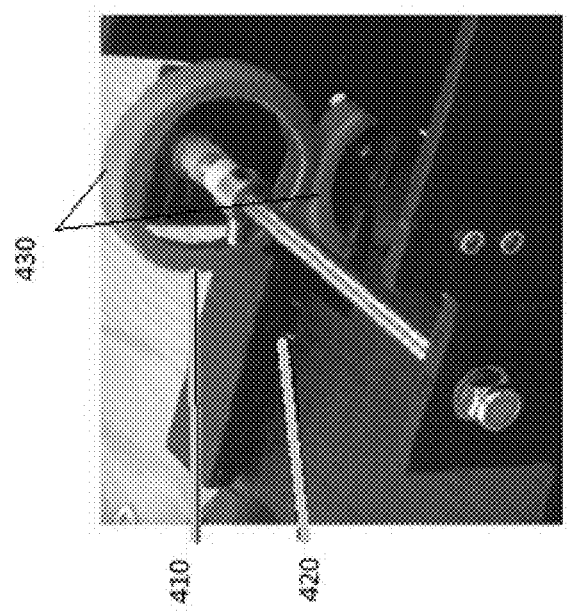

In FIGS. 4A and 4B an example embodiment of a roller assembly 410 is shown. The assembly moves the pouch packaging 320 through the device 100. The dispensing cycle may use sensors, such as infrared sensors 420, to detect the pouch package 320 location by monitoring the infrared light reflected. Two of these sensors 420 may be mounted just past the dispensing wheels 430 facing upwards, as seen in FIG. 4. The sensors may be used in closed-loop control with a motor 440 to position the next packet-edge 450 of the pouch 320 in between them for an optimal bar code 340 reading. They are also used to detect an empty cartridge 600 or potential jam in the dispensing mechanism.

As illustrated in FIG. 4B, in some embodiments there is a slot 460 for securing the roller assembly, a spring 470 for maintaining adequate tension between the rollers 430, free vertical movement and a pivot 480. The single pair of drive rollers 430 is used to grip the packages 320 on only one side, on the laminated edge 490 of the package 320. Such a configuration may be used because the contents of the packages 320 will likely jam any alternative system: the single laminated edge is the most reliable location to grip the packages 320. Even with force applied only to one edge of the roll, the pouch roll 350 will unroll straight and evenly with little to no misalignment. In some embodiments, the roller assembly may comprise more than one pair of drive rollers.

As illustrated in FIGS. 6A and 6B, the system may utilize a cartridge 600 that is designed for insertion into the cartridge receiver 150 of the device 100, or which can be manually administered. The cartridge 600 may be designed to include a child resistant cap which can be opened by an adult and may be automatically opened by the device 100 when inserted in the device 100. It will be appreciated by a person skilled in the art that the pouch packages 320 are irregularly shaped and deform easily, and as such the pouches 320 present a number of challenges, as they are prone to bunching and tearing when a roll of pouch packages 350 is pulled on from a spool.

Figure 7A:
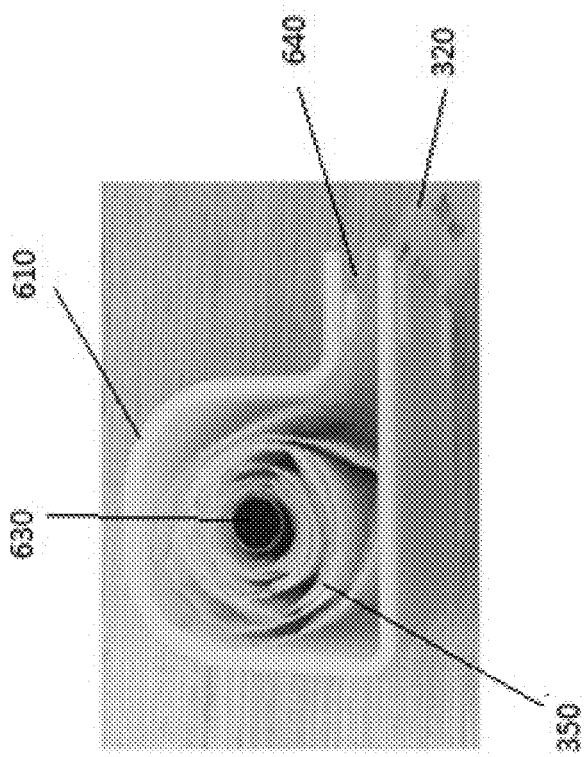
FIG. 7A shows a side view of the interior of a cartridge loaded with a roll of pouch packaging which will result in jamming of the device.
Figure 7B:
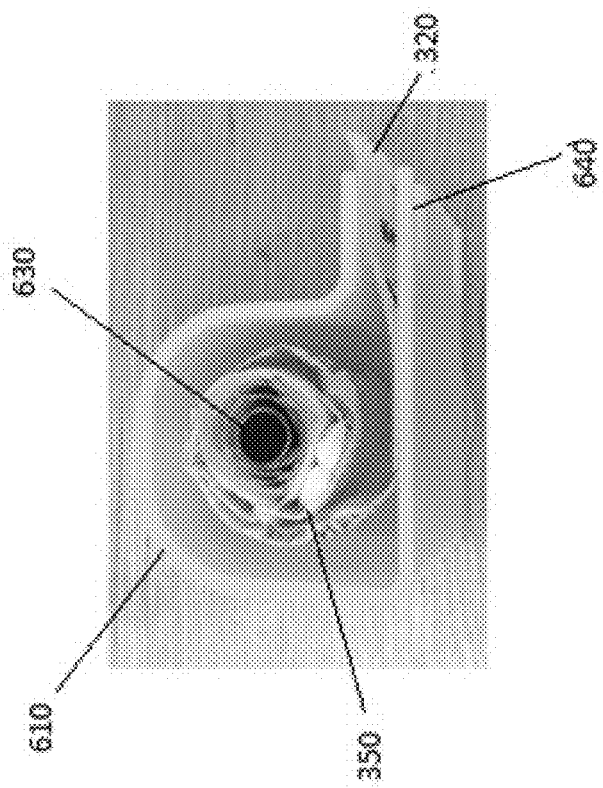
FIG. 7B shows a side view of the interior of a cartridge loaded with a roll of pouch packaging which will have a lower likelihood of jamming the device when being unrolled, according to some embodiments.

FIG. 7A shows a configuration for rolling the set of pouches 350 around the spool 630 of the cartridge 600. In the configuration shown in FIG. 7A, it has been demonstrated that the rolled set of pouches will jam or get stuck when the rollers 430 pull on the bags. Through experimentation, it has been determined that the configuration in FIG. 7B alleviates the problem of the rolled set of pouches 350 bunching or jamming when pulled by the rollers 430. The configuration in FIG. 7B, in which the rolled set of pouches 350 is pulled from the upper half of the roll (the so-called "over" configuration), results in the pouches unrolling when a pulling force is applied by the rollers. In the configuration of FIG. 7A (the so-called "under" configuration), the pulling by the rollers has the effect of causing the roll to tighten around the spool 630, which causes the roller assembly 400 to fail. Accordingly, in the embodiments disclosed herein, the configuration according to FIG. 7B should be used to increase the likelihood of correct operation. It should be noted that although the example embodiments described herein involve a horizontal axis of rotation for the spool, other embodiments are possible in which the axis of rotation can be any number of angles (e.g. vertical, oblique, etc.).

Figure 8:
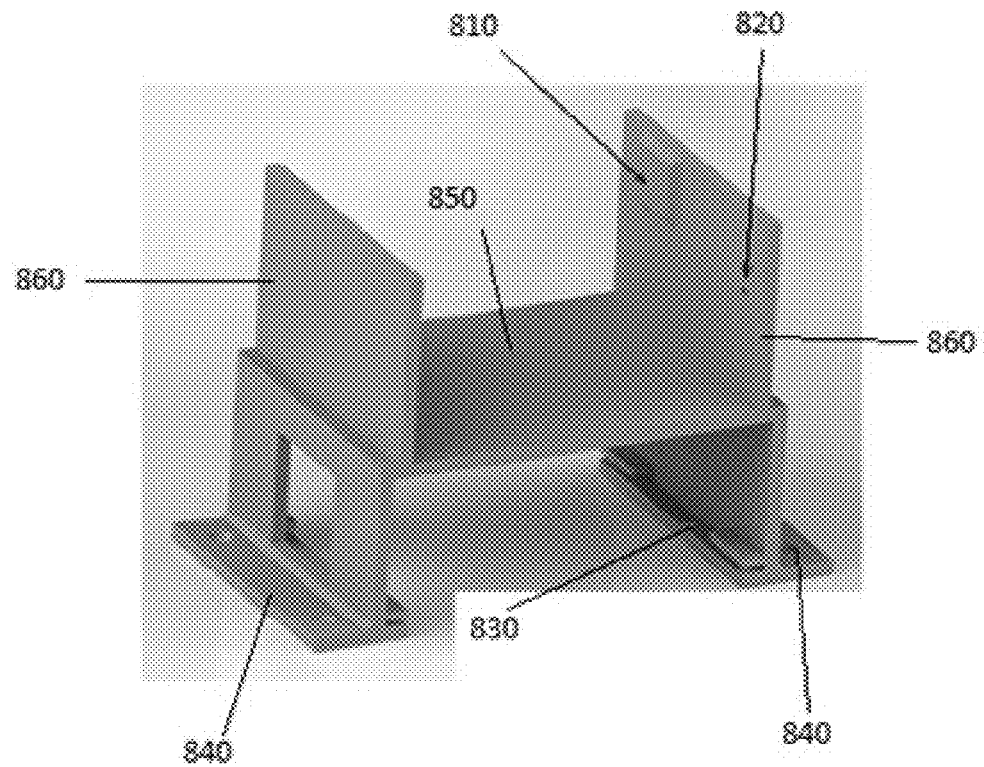
FIG. 8 is a perspective view of an example embodiment of a cartridge receiver.

FIG. 8 shows an example embodiment of a cartridge receiver 800. The receiver 800 may comprise one or more snap-in tabs 810 for securing the cartridge 600 when inserted into the receiver 800 of the device 100. In some embodiments, the receiver may comprise two T-shaped bases 840, which support a plate 850. Two side walls 860 may rest on the plate 850. In some embodiments, the bases 840, plate 850 and side walls 860 may be integrally formed. The side walls 860 may be space appropriately to allow the snap-tabs 810 to engage with the recesses 650 in the cartridge 600.

The cartridge receiver 800 may be designed to interface with two components of the device 100: the cartridge 600 and the roller assembly 410. The cartridge 600 snaps into the receiver 800 with matching tabs/recesses 810 and 650. The receiver may also contain a micro-switch 820 that may allow a microcontroller to monitor whether the cartridge 600 is in place. The cartridge 600 may then be interfaced with the roller assembly 410 utilizing the slot 660. The roller wheels 430 may fit into the slot 660 when the cartridge 600 is inserted.

Figure 9:
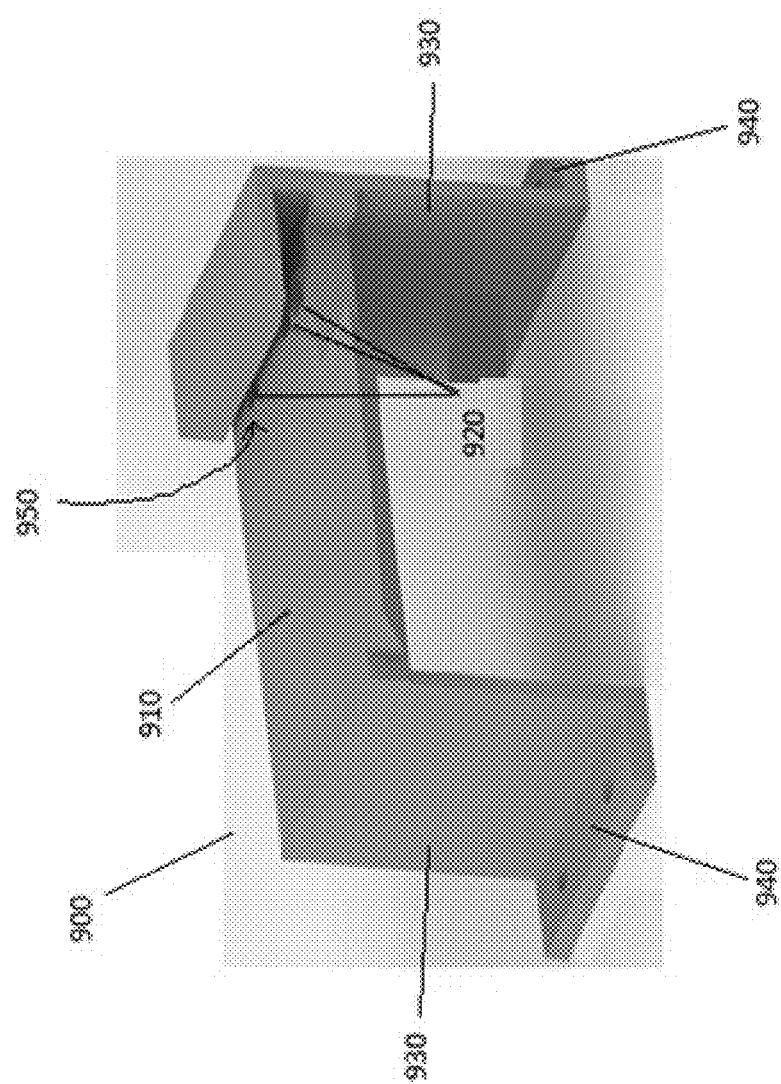
FIG. 9 is a perspective view of an example embodiment of a barcode scanning table.

FIG. 9 shows an example embodiment of a barcode scanning table 900 which may play several roles. The table 900 may interface with the roller assembly 410 to provide a flat scanning surface 910 on which the pouch package 320 may rest to facilitate successful barcode 340 scanning. The table 900 may also contain IR position sensors 920 which may assist in guiding medication pouches 320 to the opening of the device 100 from the cartridge 600. In some embodiments, the table 900 may comprise two base surfaces 940 and two support legs 930 attached thereto. The scanning surface 910 may be supported by the support legs 930, but in some embodiments, the surface 910, base 940 and legs 930 may be integrally formed. The table 950 may also comprise a notch 950 which may provide guidance for feeding an edge of a package 320 across the scanning surface 910.

As illustrated in FIG. 10A, some embodiments of the device 100 may comprise an internal camera 1010 that may work in conjunction with a mirror 1030. The camera may be adapted to read bar codes 340 printed on the pouch packaging 320 located on the scanning table 910. The camera 1010 may require a distance (e.g., 4-6 inches) to scan successfully. While it can be placed directly above the scanning table, doing so will add several inches to the overall height of the device. FIG. 10A shows one possible solution, namely using a mirror 1030 in order to reflect the light and make better use of the already available space in the device 100. As illustrated, the mirror 1030 may employ a simple 45° to the horizontal scanning table, although many angles would be suitable depending on the geometry of the configuration, and this would be apparently to a skilled person. The 45° mirror provides for an overall bend angle of 90°, as shown.

In some embodiments, which may reduce the cost of the device 100 and which may also extend the utility of the device 100, a mobile communication device (e.g., a smart phone 1040) and its external camera 1050 may be used as a substitute for the internal camera 1010 which is used in conjunction with mirror 1030 adjusted for the relevant angle position of the camera 1010 adjusted for angle of reflection.

FIG. 10B shows an example embodiment in which the mobile communication device 1040 comprises a "selfie camera" or patient-facing camera 1060, which can be used for at least two purposes. One such purpose is to, using face recognition technology in conjunction with the patient register, authentication and message server 554, authenticate the patient 1070 such that only the patient or registered authorized care workers can operate the device 100. This would protect the device 100 from being misused by children or by the wrong patient (where two or more devices 100 would potentially be in use). Another such purpose is to be able to conduct a two way video conversation.

Figure 11:
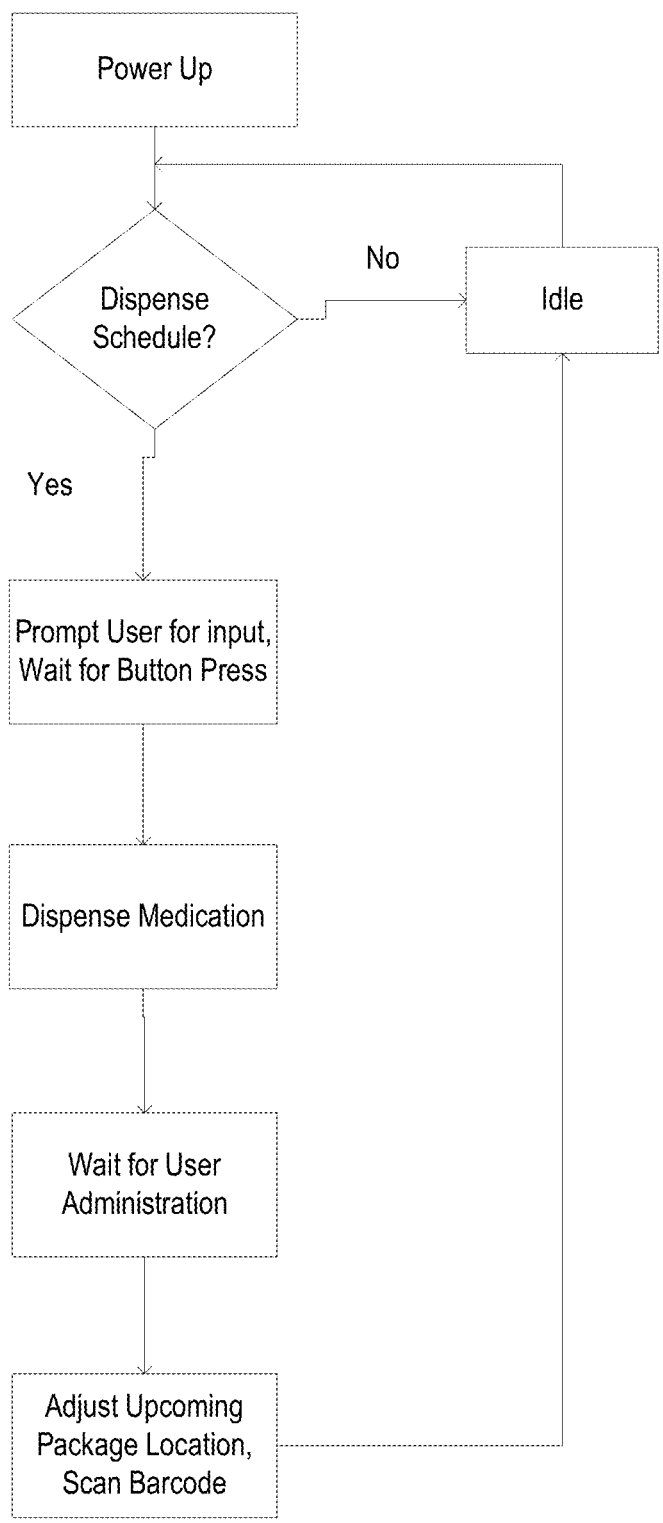
FIG. 11 is a flow chart showing an example embodiment of a method of operating a pouch dispensing device.

FIG. 11 shows an example embodiment of a flow chart for a method 1100 of operating the device 100. First, the device 100 powers up at 1110, and then receives the medication administration schedule at 1120 from a network connected device 220. Based on the schedule, when it is time to take the medication, the device 100 will prompt the patient at 1130 via sound or light to push a button to turn off the alarm, which in turn will dispense the medication pouch 320 at step 1140. In one aspect, the medication adherence monitoring device will wait or possibly prompt the patient to confirm that they have taken their medication at step 1150. The device 100 may also, as part of the dispensing process, read the current and the next bar codes 340 on the pouches 320 at step 1160 to ensure the pouches 320 are synchronized with the dispensing schedule in preparation for the next medication dispense. The device 100 may also enter an idle state at step 1170 if no schedule has been received.

Figure 12:
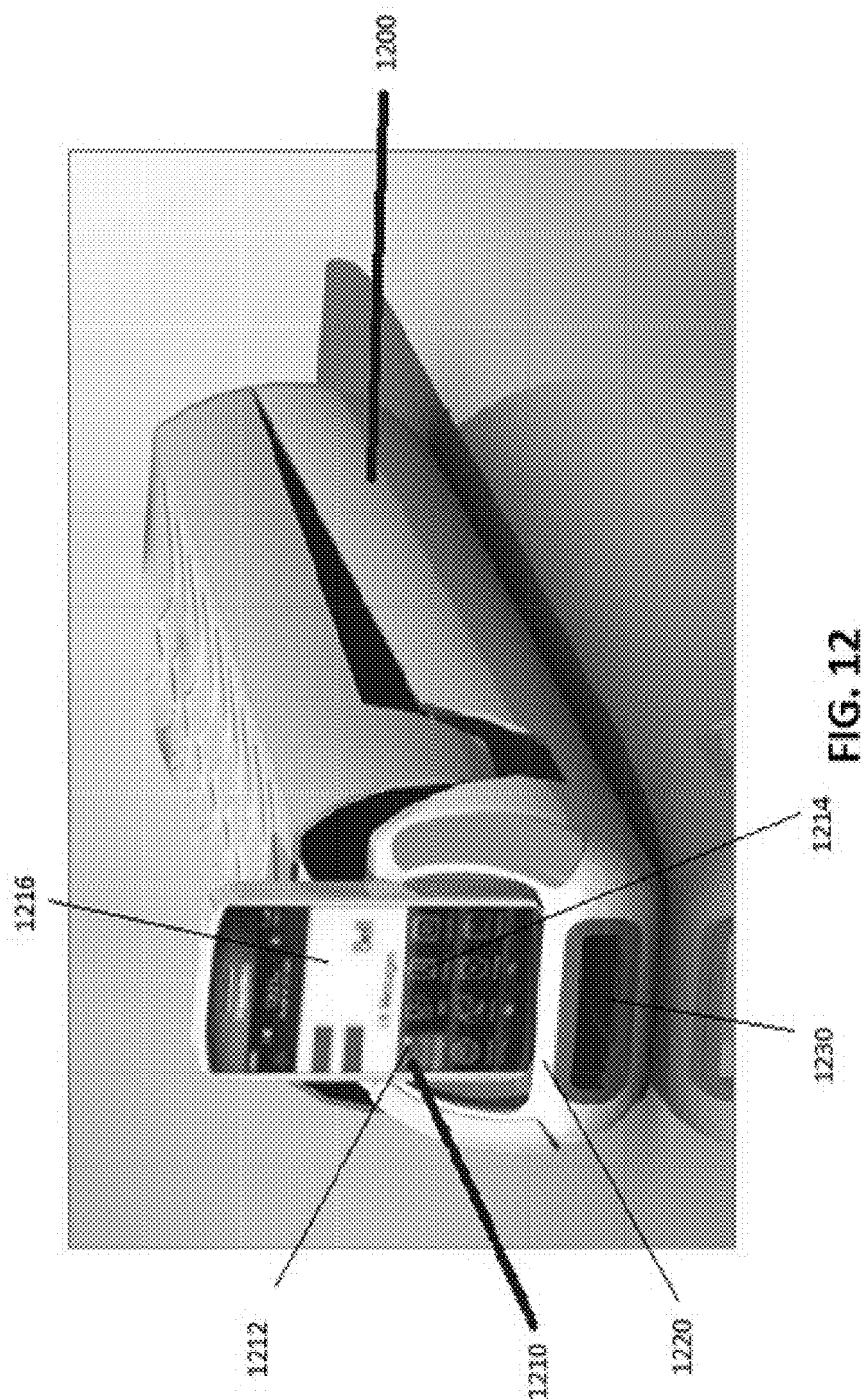
FIG. 12 illustrates an example embodiment of a dispensing device.

Another example embodiment of a medication administration device 1200 is illustrated in FIG. 12. The device 1200 may be a peripheral to a network connected device 1210. The device 1210 may include a number of features that enable this delivery of medications to a patient. These features may include the availability of input buttons 1212, 1214 or a touchscreen 1216 for accepting inputs from the patient or an authorized user. The pouch packaging may be dispensed, for example, from a dispensing slot 1230.

In FIG. 12, the medication adherence device 1200 and the networked connected device 1210 are communicatively coupled such that the device 1200 can act as a charging station (e.g. base 1220) for the network connected device 1210 and the two may be communicatively coupled either by blue tooth. USB cable or any similar connectivity standard to exchange data known in the art.

The data collected in the patient health record 546 provides valuable data that can be used by a variety of health care professionals. In some embodiments, the patient health record can be anonymized such that the privacy of the patient is preserved but the integrity of the database remains intact. In other embodiments, the patient health record may not be anonymized (for example, when data for the individual patient is being accumulated). Whether to anonymize the data is dependent upon the situation and the recipient of the data. Such records can be used for epidemiological studies, clinical trial studies and for post market surveillance of drugs approved for the market. As illustrated in FIG. 2 access to the data is provided to pharmaceutical partners 516, health care professionals 518 and drug plan insurers 520.

In some embodiments, there is a provided a device 100 which may be configured as a peripheral to a mobile communications device 1040 (e.g., a smart phone or similar network connected device), which may enable a medication adherence support and monitoring system.

For example, a computer program operable to enable individuals to interface with a network connected device 220 may be provided. The computer program may enable the individuals to be reminded when to take their medication 310, dispense the medication 310 to the individual, and provide a method for the individual to confirm that they have taken their medication 310 as well as a method to authenticate and observe the person taking their medication.

The computer program may employ a variety of techniques to support such an individual and their healthcare professionals and care givers to monitor adherence and intervene when necessary to assist the individual.

Figure 16:
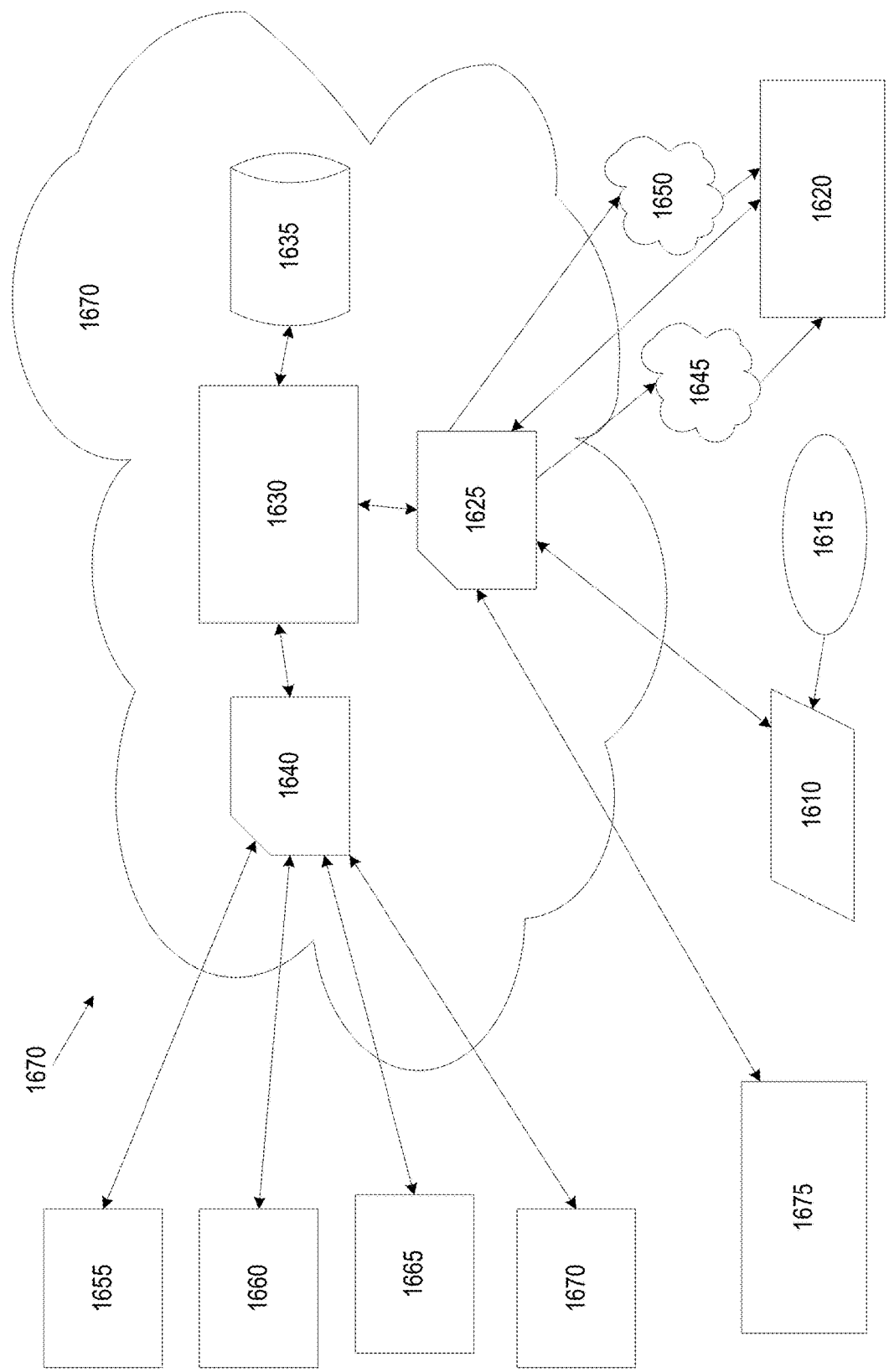
FIG. 16 is an example system architecture according to some embodiments of the invention.

The computer program may access various databases, such as a database 1635 in FIG. 16, wherein the database links to the individuals' registration information, which can include biometric information associated with the individual and may be used to authenticate the individual using the medication administration device. Biometric information may include, for example, data relating to an image of the patient's face and may be used for authentication using facial recognition techniques.

The individual may be provided with a means to confirm the authentication or override the authentication. The individual may also be provided with a means to be prompted to take a measurement associated with the medication taken and the disease state for which the medication has been prescribed.

There may also be provided a computer program operable to enable individuals to interface with a monitoring program that augments the support of the patient to include progress reporting, congratulatory and inspirational messaging as well as to inform and alert healthcare professionals and care givers of patient response to medication, progress in the management of the relevant diseases and to provide alerts when intervention is required.

In some embodiments, internal memory is provided so that a device can store information independent of the system. For example, compliance data may be stored in memory until the phone 1210 is Bluetooth™ connected and data may be synced to the phone 1210, and an internal clock may be used to issue reminders independently.

Figure 13:
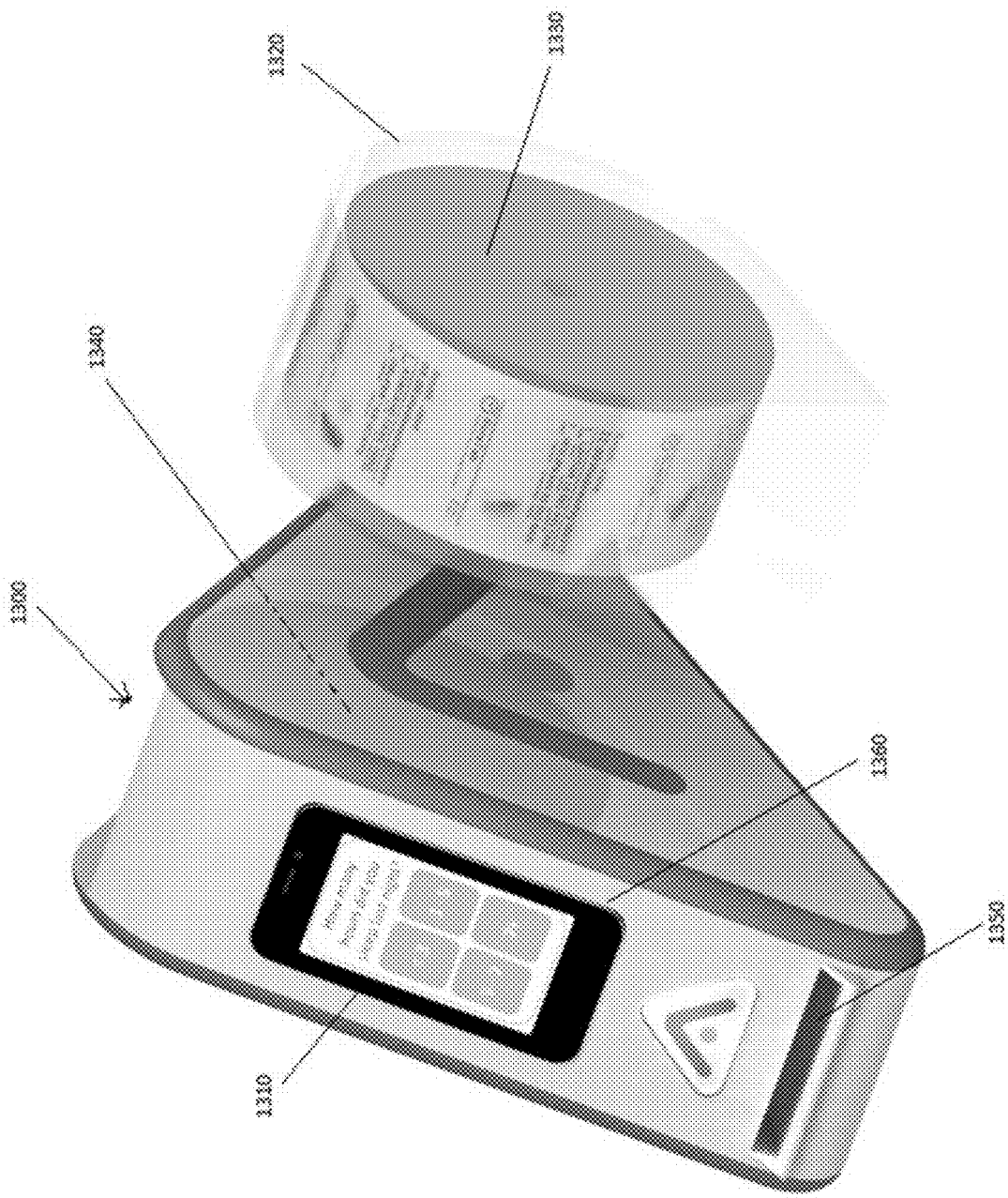
FIG. 13 is a perspective view of another example embodiment of a dispensing device.

FIG. 13 provides a perspective view of another example embodiment of a dispensing device 1300. Here, a mobile communications device 1310 is physically coupled to the device 1300. The device 1300 may have a recess 1360 adapted to accommodate the mobile device 1310, and may optionally serve as a charging base for charging the battery of the mobile device. Many charging mechanisms are known in the art and may include, for example, wired charging through charging cables and adapters, or wireless charging (e.g. the Qi™ inductive power standard for mobile devices which have that capability). In some embodiments, the recess 1360 may provide an appropriate angle for the mobile device to be pointing upward towards the face of the user. This may enable faster authentication through use of the camera 1360 in the mobile device 1310 for facial recognition purposes.

As shown in FIG. 13, the device 1300 also comprises a cartridge 1320 which is loaded with a roll of medication pouches 1330 as previously described. The cartridge 1320 may be loaded and secured into a receiving portion 1340 of the device 1300. The device 1300 may also comprise a slot 1350 from which the pouches 1330 may be dispensed. The device 1300 may also comprise a power source, such as an AC adapter or a battery (not illustrated) for operating all of the components which require a power source.

Figure 14:
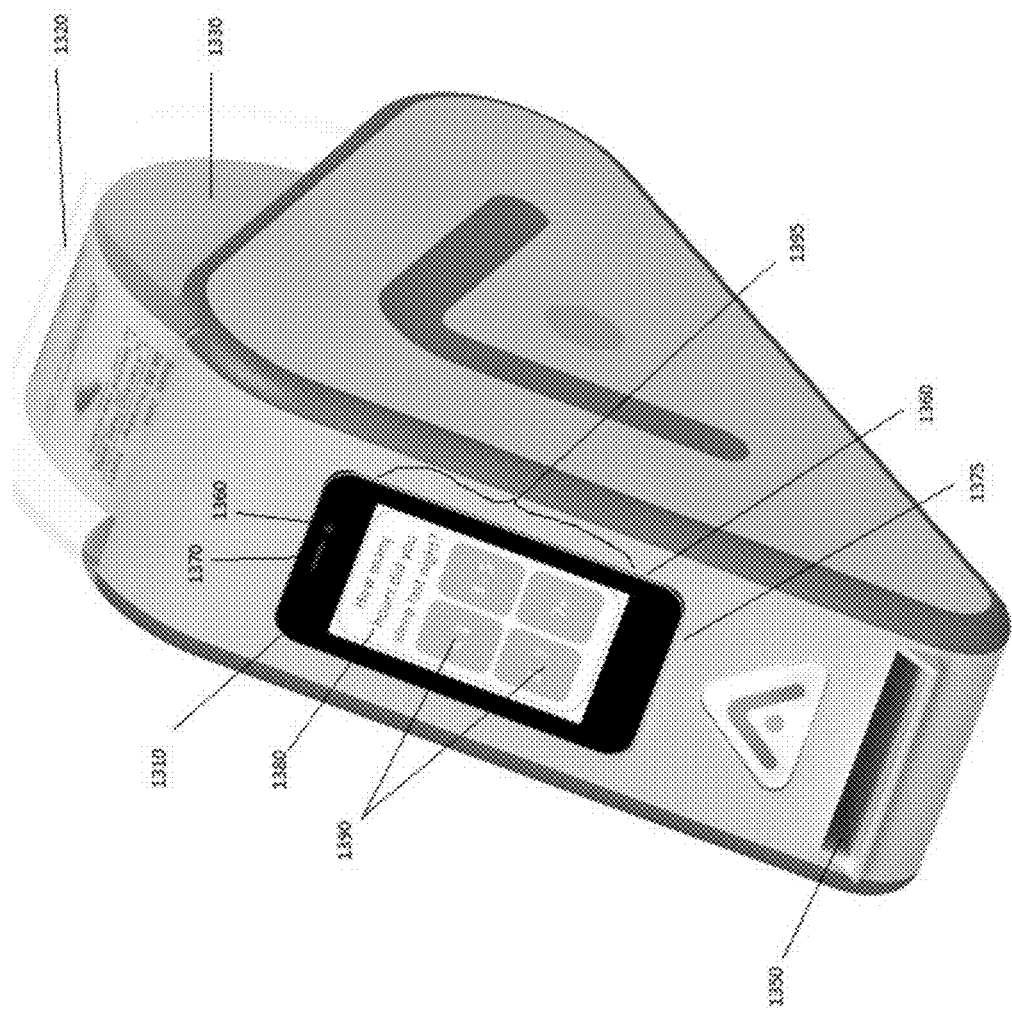
FIG. 14 is a perspective view of the example dispensing device from FIG. 13 in which the cartridge has been loaded into the device.

FIG. 14 provides a perspective view of the device 1300 in which the cartridge 1320 has been loaded into the receiving portion 1340 of the device 1300 and the pouches 1330 are ready for dispensing from the slot 1350. It is to be appreciated that the mobile device 1310 may comprise a touchscreen 1395 which may both accept inputs from the patient or authorized user, as well as display information (e.g. alerts or other messages for the patient or care giver). For example, in some embodiments, the touchscreen 1395 may serve as an alarm which notifies the patient that it is time to take their medication. The touchscreen 1395 may also serve as the input for disabling the alarm, and for instructing the device 1300 to dispense a medication pouch 1330 in accordance with the medication schedule.

Further, the mobile device 1310 may comprise a camera 1360, a speaker 1370, and a microphone 1375 through which video conferences may be conducted with health care professionals, care givers, or the like. It is to be appreciated that the camera 1360 on the mobile device 1310 may be utilized to authenticate the user of the device using facial recognition in order to confirm that the user is either a patient or the authorized user of the device. This may be accomplished by obtaining biometric information relating to the patient or authorized user from a database using, for example, information contained within the medication schedule or bar codes found on the pouch (which should match the information in the medication schedule in order for the device 1300 to function correctly). The mobile device 1310 may also comprise a rear-facing camera (as shown, for example, in element 1050 of FIG. 10B) on the back end, which may be used to scan the bar codes on pouch packaging during the dispensing process. Such scanning may or may not include mirrors as shown in FIGS. 10A and 10B, and a person skilled in the art will appreciate that many configurations are possible in which the rear-facing camera of a mobile device could be used to capture image data from the bar codes on pouch packaging 1330.

Further, it is to be appreciated that the mobile device 1310 may prompt the user for information before, after, or while medication is being administered. In FIG. 14, the touchscreen 1395 is displaying a question 1380 ("How many hours did you sleep last night?") and is prompting the user for an input. In some embodiments, the mobile device may provide a set of predetermined responses 1390 from which the patient or caregiver may select the appropriate response. In other embodiments, the user may be given the option of entering a specific response into the mobile device rather than selecting from predetermined options 1390. Such patient response data may be stored by the device in a memory, or stored by the mobile device 1310 in memory, and may also be communicated to a server of a third party, by one or more of the dispensing device and the mobile device. Examples of third parties include, but are not limited to, pharmaceutical companies, healthcare providers, pharmacy networks, care givers, physicians, etc.

It should also be noted in FIGS. 13 and 14 that although the mobile device 1310 is illustrated as being docked in the receiving portion 1360 of the device 1300, in other embodiments the system is capable of the same functionality even when the mobile device 1310 is not docked in the receiving portion 1360. For example, a wireless network connection of the many varieties known in the art may be established between the mobile device 1310 and the device 1300, and the same functionality can be implemented without the mobile device 1310 and device 1300 being in physical contact with one another.

It should be appreciated that in some embodiments, the device 1300 can be viewed as a peripheral device which is commanded by the mobile device 1310. In some embodiments, this may result in the cost of the device decreasing, as the functionality and processing capabilities may be off-loaded onto the mobile device 1310 and associated network-connected entities rather than having to implement all of the functionality in the device 1300 itself.

In some embodiments, every time medication is dispensed from the device 1300, that data may be recorded. This data may be recorded to the memory in the device 1300, or the memory in mobile device 1310. The device 1300 or the mobile device 1310 may comprise a transceiver for transmitting this data to a third party. In some embodiments, this data may be anonymized, and in other embodiments the data is not anonymized. This data may include, for example, the date, the time, and the drug dispensed and may form part of a comprehensive compliance record. Thus, some embodiments of the present invention may enable real-time patient reported outcomes. This may be accomplished, for example, by prompting the patient to answer multiple-choice questions as described above. A drug company may configure the mobile device 1310 to ask any amount of customized questions which are relevant to the trial. Such response data may be correlated with how consistently the patient has taken their medication, which may create a valuable and/or useful data set which has previously not been available to researchers.

Some embodiments of the present invention may be used in clinical trial research, which may enable, for example, pharmaceutical companies to collect compliance data, and real-time patient reported outcomes from some or every patient for the entire duration a clinical trial. This may allow for an in-depth study on how the medication works on a strict schedule versus an inconsistent one. It may even allow a drug company to disqualify patients who have missed too many doses. This may help in ensuring the quality of the data obtained from a clinical trial.

Some embodiments of the invention may provide one or more of the following functionality: a) automated compliance data collection, b) remotely recording the date and time of administered medication, c) greater accuracy in collected data, d) identification of strict adherence to medication schedules vs inconsistent adherence, e) excluding results of non-compliant patients, f) collecting patient data at the time of drug administration, g) asking customized questions throughout a trial, and h) the ability to correlate patient feedback with adherence data.

It should also be noted that some embodiments of the invention may be useful in settings such as, for example, retirement and long-term care facilities. It is commonplace at such facilities for medication to be dispensed to individuals manually, which can result quite easily in medications being mixed up, or misplaced, or administered to the wrong patient. Some embodiments of the present invention may aid in preventing such outcomes at such facilities, as the identity of a patient can be authenticated prior to the dispensing of medication. The sounding of alarms may provide further helpful reminders to patients that medication should be taken.

Figure 15:
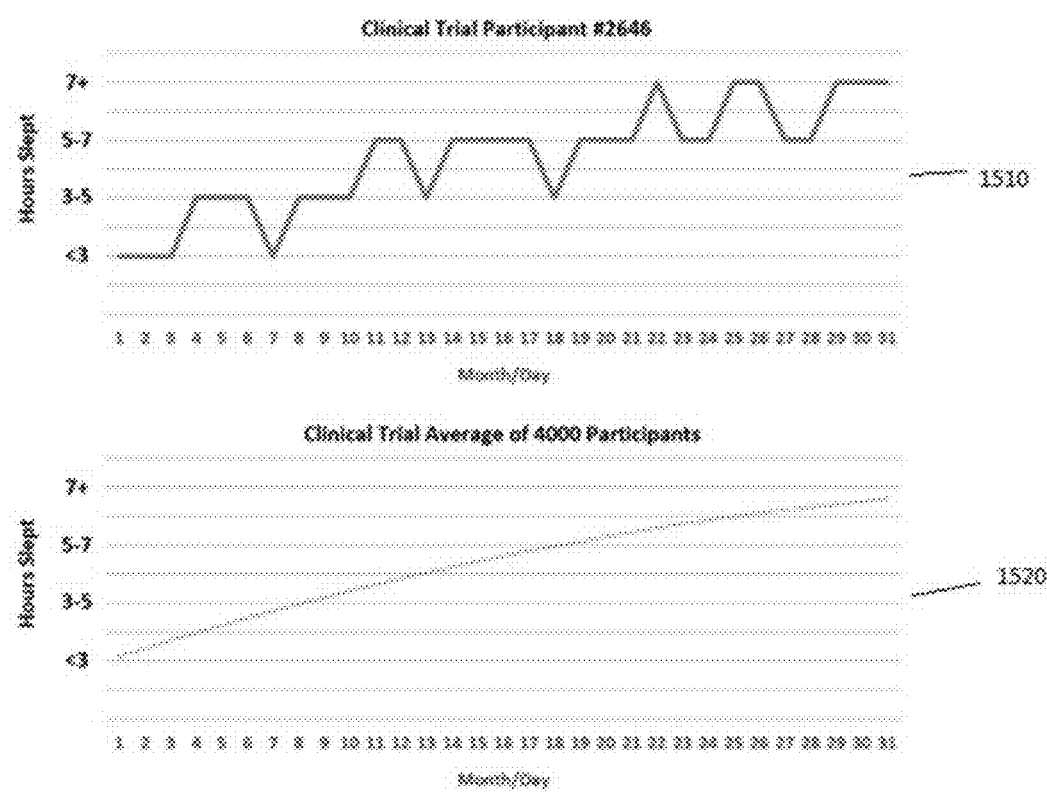
FIG. 15 is an example illustration of reported patient outcome data which may be collected according to some embodiments.

FIG. 15 shows example data representations of the patient response data that may be collected by the device 1300 in cooperation with the mobile device 1310, and related analyses of the data. Such patient response data may be used to evaluate the efficacy of a medication for an individual user, as shown in the graph 1510. Such graphs may come in a variety of forms and may track a number of variables, and are not limited to the comparison of number of hours slept vs. time as shown in FIG. 15. A person skilled in the art will appreciate that graph 1510 is merely an example of the type of data that may be gathered and analyzed. The type of data collected may be customized by, for example, a company running a clinical trial (in order to ascertain the relevant measurements), a pharmaceutical company (to ascertain efficacy or possible side effects), or the doctor or pharmacist, just to name a few. In some embodiments, such data can be communicated to various third parties (e.g. pharmaceutical companies, pharmacies, research companies, clinical trial providers, etc.).

Such patient data may also be aggregated and used to ascertain data and trends for groups of patients, as shown in graph 1520. In some embodiments, the individual patient data may be anonymized prior to transmitting the patient data to the entity which aggregates the data.

FIG. 16 illustrates an example embodiment of a system architecture 1600 which may be used to communicate some or all of the data described herein. The medication 1615 is identified though both the medication schedule and the bar codes on the pouch packaging. In some embodiments, the schedule is received on a mobile device from a pharmacy or pharmacy management system. This information can be stored on system hardware 1610 (for example, a memory in the dispensing device, or in a mobile device which can be communicatively coupled to the dispensing device). The hardware 1610 may communicate data with other components via cloud components 1680. The hardware may communicate with a secure API 1625, which may then push messages and notifications to mobile apps 1620 running on mobile devices. These messages may be transmitted using, for example, Google™ cloud messaging service 1645 or Apple™ push notification service 1650, or any other messaging service known to a person skilled in the art. The API 1625 may ensure secure communication between devices, and may also provide a communication link to a backend server 1630. The backend server may need to have functionality and security features which comply with domestic laws (e.g. the *Personal Information Protection and Electronic Documents Act* in Canada, the *Health Insurance Portability and Accountability Act* and 21 CFR Part 11 compliance for Clinical Trial Electronic Records in the United States of America). The backend server 1630 may provide a communication link with a database 1635 in which various patient data may be stored. The backend server may also provide a communication link to a second secure API 1640 which enables secure communication with, for example, clinical trial management system 1655, pharmacy management system 1660, home care company system 1665, and residential care facility system 1670. The secure API 1625 may also enable secure communication with an administrator web app 1675 which may manage the questions displayed to the user, both pre-dispensing and post-dispensing, as well as track the distribution of data to external parties, and run data integrity checks for compliance, and the like. The communication links described herein may be bilateral and allow communications in both directions, or may also be unidirectional. A person skilled in the art would consider many factors in implementing a particular design.

Figure 17:
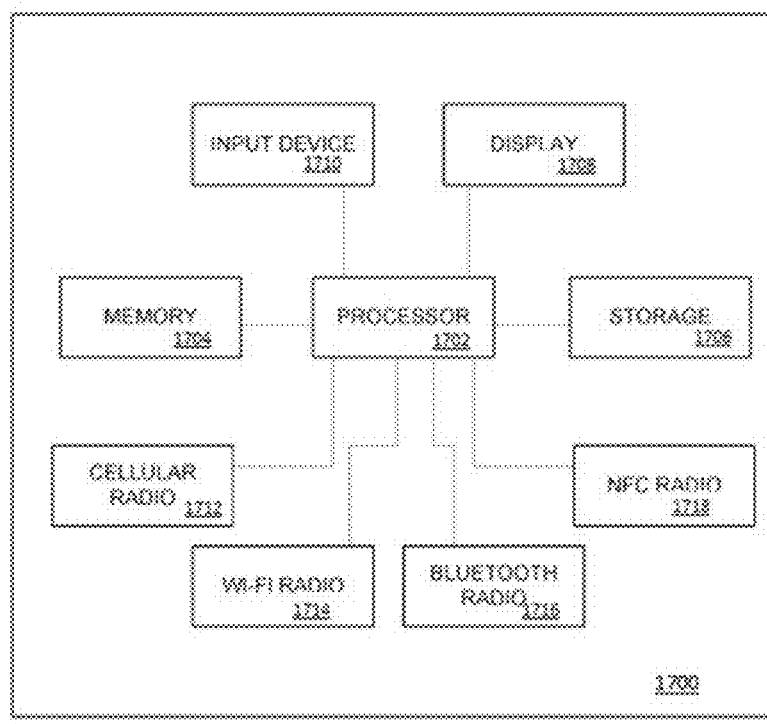
FIG. 17 is a schematic diagram of a mobile communication device.

FIG. 17 depicts a schematic diagram of an example mobile communication device 1700. As depicted, mobile communication device 1700 is a smartphone.

Mobile device 1700 includes a processor 1702. Processor 1702 may be an Intel x86 processor. ARM processor or the like. Processor 1702 is interconnected with a memory 1704 and persistent storage 1706. Processor 1702 is further interconnected with one or more display devices 1708 and one or more input devices 1710, such as a touch-sensitive panel, keyboard, or the like.

Processor 1702 may further be interconnected with a plurality of communications radios. For example, mobile communication device 1700 may have at least one cellular radio 1712 for voice or data communications on a wireless network. Processor 1702 may also be interconnected with a WI-FI radio 1714, a bluetooth radio 1716 and a near-field communication (NFC) radio 1718.

Cellular radio 1710 may be operable, for example, interface mobile communication device 1700 to a 2G/3G/4G/ LTE GSM or CDMA cellular network. WI-FI radio 1714 may be operable to wirelessly interface mobile communication device 1700 to a local-area network, for example, using IEEE 802.11a/b/g/n/ac standards. Bluetooth radio 1716 may be operable to interface mobile communication device 1700 with neighboring bluetooth devices according to a bluetooth protocol. NFC radio 1718 may be operable to behave in any of a plurality of standard NFC protocols. NFC radio 1718 may be capable of operating in a plurality of different modes, including NFC card emulation modes, NFC reader/writer modes and NFC peer-to-peer modes. One or more of cellular radio 1710, wi-fi radio 1714, Bluetooth radio 1716 and NFC radio 1718 may be capable of receiving signals according to corresponding wireless communication protocols and reporting an associated signal strength.

In some embodiments, one or more components of mobile communication device 1702 may be formed as portions of a single semiconductor die, referred to as a "system-on-chip". Alternatively, components may be formed as separate semiconductor dies, in communication through one or more buses on a circuit board.

Figure 18:
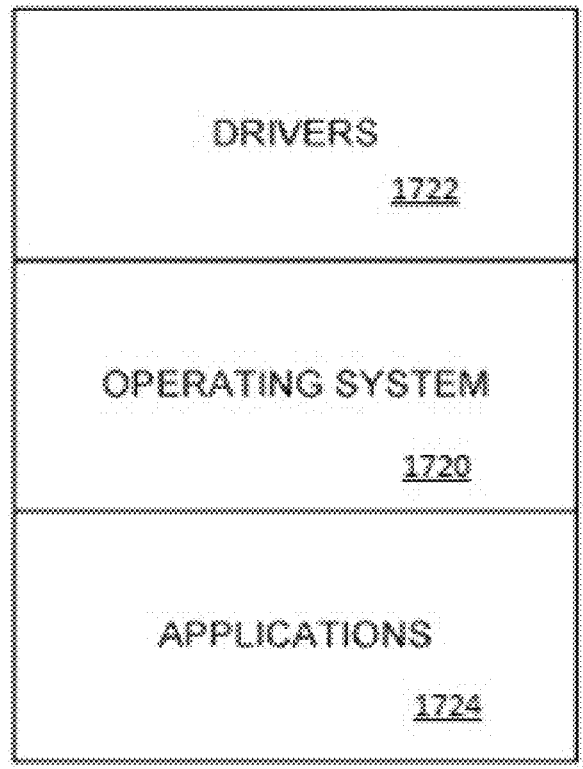
FIG. 18 is a block diagram showing software applications of the mobile communication device of FIG. 17.

Mobile device 1700 may operate under control of software stored on storage 106 and executed by processor 1702. FIG. 18 depicts example software components.

Software components may include an operating system 1720, such as Apple™ iOS™, Android™, Microsoft™ Windows™ Linux or the like. Operating system 1720 may interface with hardware components of mobile communication device 1700 by way of drivers 1722. A plurality of applications 1724 may run within operating software 1720. Operating system 1720 may provide applications 1724 with access to low-level (e.g. hardware) functions of mobile communication device 1700 by way of application programming interfaces (APIs).

By way of example, applications 1724 may include a phone dialer, an email client, an internet browser, messaging applications, social media applications, media players, and the like. Applications 1724 may further include one or more settings applications for controlling functions of mobile communication device 1720. The settings applications may, for example, toggle components such as cellular radio 1710, Wi-Fi radio 1712, Bluetooth radio 1714 and NFC radio 1716 ON or OFF. The settings applications may further enable or disable other applications from running, or enable or disable specific files or file types from being opened.

The settings applications may be operable in response to user input, for example, touching a button or screen, or to an event such as a received message, data transmission, signal or the like. Settings may therefore be altered in response to a transmission received on any of cellular radio 1712. Wi-Fi radio 1714. Bluetooth radio 1716 or NFC radio 1718. The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

In some embodiments, the applications 1724 may include a medication management application. Medication management application may be operable to receive signals from a radio source such as NFC radio 1718. Bluetooth radio 1716, Wi-Fi radio 1714 or cellular radio 1712. Medication management application may also be operable to access and change settings of other applications 1724 or of operating system 1720. For example, the medication management application may be operable to receive a set of questions from a transmission received from a radio source and display the questions on the display 1708 and receive input from the patient on, for example, the touchscreen input device 1710.

Figure 19:
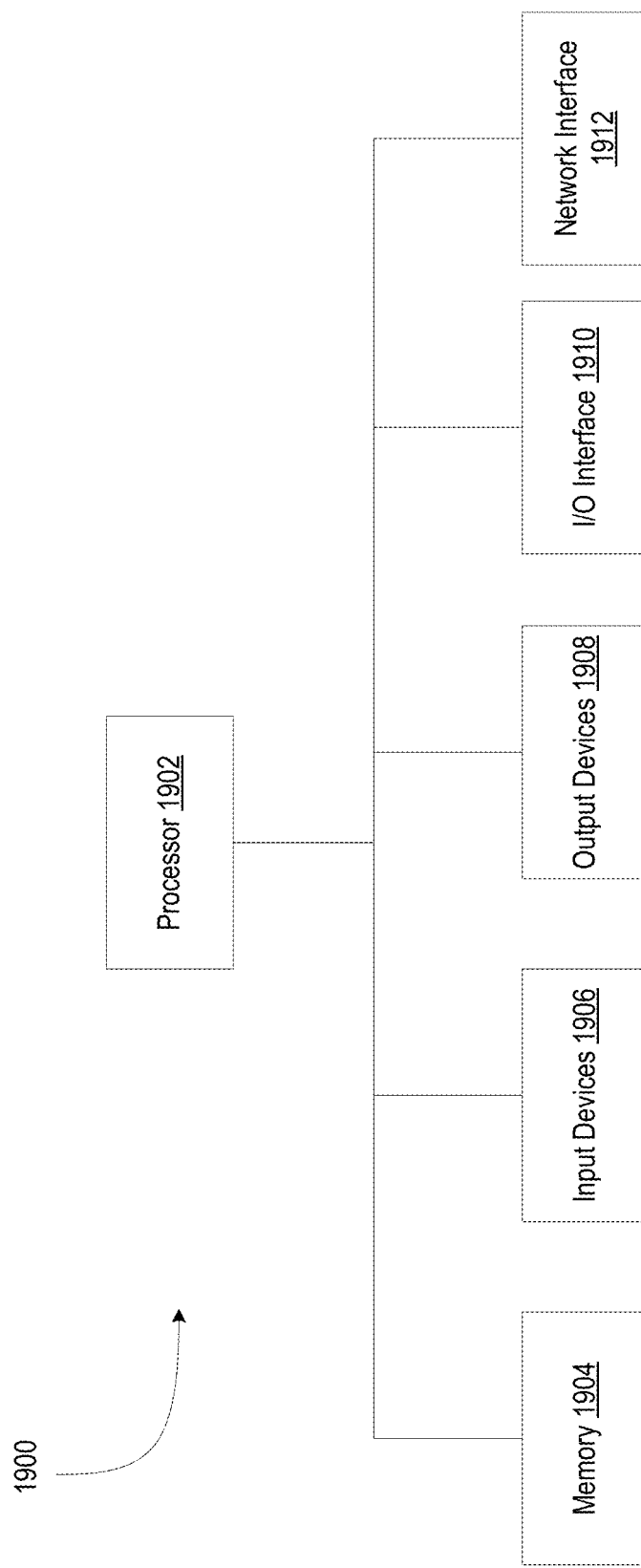
FIG. 19 is a block diagram showing components of an example embodiment of a dispensing device.

FIG. 19 is a block diagram of components of an example medication dispensing device 1900. As depicted, the medication dispensing device 1900 may comprise a processor 1902, memory 1904, input devices 1906, output devices 1908. I/O interface 1910, and network interface 1912.

Processor 1902 may be an Intel or AMD x86 or x64, PowerPC, ARM processor, or the like. Processor 1902 may operate under control of software loaded in memory 1904. Network interface 1912 connects the dispensing device 1900 to networks. I/O interface 1910 connects the device 1900 to input devices 1906 and output devices 1908. Input devices 1906 may include, for example, peripherals such as a mouse, keyboard. USB devices, cameras, user-activated buttons or the like. Output devices 1908 may include, for example, displays, touchscreens, alarm lights and speakers, and components such as motors for driving dispensing mechanisms. The network interface 1912 may further comprise a transceiver which allows the device 1900 to transmit data from memory to other recipients. The network interface 1912 may also enable the device 1900 to communicate with a mobile device 1700 through either wired or wireless communication protocols.

It should be appreciated that although FIG. 19 shows all of these components, it is possible that in some embodiments, one or more of these components are implemented on a mobile device 1700. This may include, for example, input devices such as capacitive touch input devices, memory for storing patient data, and output devices such as a display which may work in conjunction with the touchscreen to prompt a user for an input and then receive an input from the user in response. The mobile device 1700 may also use a transceiver through a cellular radio, Wi-Fi radio, Bluetooth radio, NFC radio or the like to transmit stored data to other recipients. Such recipients may include, for example, researchers, pharmaceutical companies, or the like.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, or combinations thereof.

Throughout the foregoing discussion, numerous references will have been made regarding servers, services, interfaces, portals, platforms, or other systems formed from computing devices. It will be appreciated by persons skilled in the art that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The term "connected" or "coupled to" may include both direct coupling (in which two elements that are coupled to each other contact each other) and indirect coupling (in which at least one additional element is located between the two elements).

Some embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computing device (personal computer, server, or network device) to execute the methods provided by the embodiments.

Some of the embodiments described herein may be implemented in part with physical computer hardware, including computing devices, servers, receivers, transmitters, processors, memory, displays, and networks. The embodiments described herein provide useful physical machines and particularly configured computer hardware arrangements.

The embodiments described herein are directed to electronic machines and methods implemented by electronic machines adapted for processing and transforming electromagnetic signals which represent various types of information.

The embodiments described herein pervasively and integrally relate to machines, and their uses; and the embodiments described herein have no meaning or practical applicability outside their use with computer hardware, machines, and various hardware components. Substituting the physical hardware particularly configured to implement various acts for non-physical hardware; using mental steps for example, may substantially affect the way the embodiments work.

Such computer hardware limitations are clearly essential elements of the embodiments described herein, and they cannot be omitted or substituted for mental means without having a material effect on the operation and structure of the embodiments described herein. The computer hardware is essential to implement the various embodiments described herein and is not merely used to perform steps expeditiously and in an efficient manner.

Although the embodiments have been described in detail, it should be understood that various changes, substitutions and alterations can be made herein without departing from the scope as defined by the appended claims.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized. Accordingly, the appended claims are intended to include within their scope such processes, machines, manufacture, compositions of matter, means, methods, or steps.

As can be understood, the examples described above and illustrated are intended to be exemplary only. The claims are not to be limited to the specific examples described herein, but should be given the broadest interpretation consistent with the application as a whole.

What is claimed is:

1. An apparatus for managing adherence to medication by a patient, the apparatus comprising: a processor; a memory storing a predefined first medication schedule; an alert system configured to notify the patient to take medication, wherein the alert system is activated based on the predefined first medication schedule stored in the memory; a dispensing unit configured to dispense a pouch containing one or more medications, the pouch having displayed thereon machine-readable indicia representing a part of a second medication schedule; and an input configured to receive from a user an instruction to dispense the pouch, wherein the instruction to dispense deactivates the alert system and causes a scanning device to scan the indicia on the pouch to be dispensed, wherein the processor is configured to extract the part of the second medication schedule represented by the scanned indicia and compare the part of the second medication schedule to the predefined first medication schedule, and wherein the pouch is dispensed by the dispensing unit if the part of the second medication schedule is determined from the comparing to have a match with the predefined first medication schedule.

2. The apparatus of claim 1, wherein said input is further configured to receive a confirmation command indicating that the medication has been taken by the patient.

3. The apparatus of claim 1, wherein data relating to dispensing of the medication is automatically stored in the memory.

4. The apparatus of claim 1, further comprising an output configured to prompt the user for data relating to the patient.

5. The apparatus of claim 1, wherein the input is further configured to receive data relating to the patient.

6. The apparatus of claim 5, wherein the data relating to the patient comprises at least one of a) the date and time of a dose of the medication, b) patient reported outcomes, and c) compliance data.

7. The apparatus of claim 6, wherein the data relating to the patient is stored in a database as the patient data is collected.

8. The apparatus of claim 1, wherein at least one of the alert system, the input, and the scanning device is embodied on a mobile communication device that is communicatively coupled to the apparatus.

9. The apparatus of claim 1, wherein an identity of the user is authenticated using a camera, wherein the authenticating comprises obtaining an image of a face of the user and using the processor to compare the image of the face of the user to an image of at least one of the patient and authorized users through facial recognition.

10. The apparatus of claim 1, wherein the pouch is stored in a removable cartridge, wherein the dispensing unit is configured to receive the cartridge.

11. The apparatus of claim 10, wherein the cartridge comprises an enclosure and a spool, wherein the pouch is one of a plurality of pouches wound around the spool into a roll and the pouch being dispensed is pulled from the roll.

12. The apparatus of claim 1, wherein the dispensing unit comprises a roller assembly having at least two sensors and a motor, wherein a position of the pouch being dispensed is controlled by the motor based on outputs of the at least two sensors, and wherein the roller assembly further comprises two rollers, wherein the two rollers are configured to engage a laminated edge of the pouch being dispensed.

13. The apparatus of claim 11, wherein the enclosure comprises a plurality of recesses adapted to enter into frictional engagement with a plurality of protrusions on the dispensing unit.

14. The apparatus of claim 5, further comprising a transceiver configured to transmit the data relating to the patient to one or more recipients.

15. The apparatus of claim 14, wherein the transceiver is embodied on a mobile communication device that is communicatively coupled to the apparatus.

16. The apparatus of claim 5, wherein the data relating to the patient is stored on a mobile communication device that is communicatively coupled to the apparatus.

17. The apparatus of claim 1, wherein the predefined medication schedule stored in the memory is received from a pharmacy management system.

18. The apparatus of claim 14, wherein the data relating to the patient is encrypted prior to transmission.

19. A method of managing adherence to medication by a patient, the method comprising: receiving a predefined first medication schedule; storing the predefined first medication schedule on a memory of a dispensing device; activating an alert system based on the predefined first medication schedule; receiving an instruction from a user to dispense, from the dispensing device, a pouch containing a medication, the pouch having displayed thereon a machine-readable indicia representing a part of a second medication schedule; responsive to receiving the instruction to dispense, deactivating the alert system; scanning the indicia on the pouch to be dispensed; extracting the part of the second medication schedule represented by the scanned indicia; comparing the part of the second medication schedule to the predefined first medication schedule; and dispensing the pouch from the dispensing unit if the part of the second medication schedule is determined from the comparing to have a match with the predefined first medication schedule.

20. The method of claim 19, wherein receiving the predefined first medication schedule comprises receiving the predefined first medication schedule on a mobile device from a pharmacy management system.

21. The method of claim 19, further comprising authenticating an identity of the user by obtaining, using a camera, an image of a face of the user, and using facial recognition to determine that the face of the user matches a face of the patient or a face of an authorized user.

22. The method of claim 19, further comprising receiving confirmation that the medication was taken by the patient.

23. The method of claim 19, further comprising: rolling the pouch into a roll with a plurality of other pouches in a cartridge; and loading the cartridge into a dispensing unit, wherein the dispensing comprises pulling, using the dispensing unit, the pouch from the roll.

24. The method of claim 19, further comprising prompting the user for data relating to the patient.

25. The method of claim 19, further comprising receiving data relating to the patient after the medication has been taken by the patient.

26. The method of claim 25, further comprising storing the received data relating to the patient on a mobile communication device.

27. The method of claim 25, further comprising transmitting the received data relating to the patient to one or more recipients.

28. The method of claim 27, further comprising encrypting the received data relating to the patient prior to the transmitting.

29. The method of claim 19, wherein receiving the instruction to dispense the pouch comprises receiving the instruction on a mobile device that is communicatively coupled to the dispensing unit.

30. A non-transitory computer-readable storage medium having stored thereon computer executable instructions that, when executed by a processor, cause the processor to perform the method of claim 19.

31. The apparatus of claim 4, wherein the output is embodied on a mobile communication device that is communicatively coupled to the apparatus.

* * * * *